(12) United States Patent
Hinman et al.

(10) Patent No.: US 9,561,045 B2
(45) Date of Patent: Feb. 7, 2017

(54) TOOL WITH ROTATION LOCK

(75) Inventors: Cameron D. Hinman, Thurmond, NC (US); David J. Danitz, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 569 days.

(21) Appl. No.: 11/787,607

(22) Filed: Apr. 16, 2007

(65) Prior Publication Data

US 2007/0287993 A1    Dec. 13, 2007

Related U.S. Application Data

(60) Provisional application No. 60/813,650, filed on Jun. 13, 2006.

(51) Int. Cl.
 *A61B 17/00* (2006.01)
 *A61B 17/29* (2006.01)
 *A61B 17/062* (2006.01)

(52) U.S. Cl.
 CPC ............. *A61B 17/29* (2013.01); *A61B 17/062* (2013.01); *A61B 2017/2927* (2013.01); *A61B 2017/2929* (2013.01); *A61B 2017/2946* (2013.01)

(58) Field of Classification Search
 CPC ............... A61B 2017/2927; A61B 2017/2905; A61B 1/0055; A61B 2017/003; A61B 2017/2929; A61B 2017/291; A61B 2017/00323; A61B 2017/00327; A61B 2019/2238; A61B 2019/2242; A61B 19/22; A61B 2017/292; A61B 2017/2946; A61B 2019/266
(Continued)

(56) References Cited

U.S. PATENT DOCUMENTS 1,820,463 A  8/1931 Klein
3,060,972 A  10/1962 Sheldon
(Continued)

FOREIGN PATENT DOCUMENTS

DE  10132358 A1  1/2003
EP  0 165 718    12/1985
(Continued)

OTHER PUBLICATIONS

Hegeman et al; U.S. Appl. No. 11/787,543 entitled "Tool with articulation lock," filed Apr. 16, 2007.
(Continued)

*Primary Examiner* — Anhtuan T Nguyen
*Assistant Examiner* — Alexandra Newton

(57) ABSTRACT

The invention provides surgical or diagnostic tools and associated methods that offer improved user control for operating remotely within regions of the body. These tools include a proximally-located actuator for the operation of a distal end effector, as well as proximally-located actuators for articulational and rotational movements of the end effector. Control mechanisms and methods refine operator control of end effector actuation and of these articulational and rotational movements. A rotation lock provides for enablement and disablement of rotatability of the end effector. The tool may also include other features. A multi-state ratchet for end effector actuation provides enablement-disablement options with tactile feedback. A force limiter mechanism protects the end effector and manipulated objects from the harm of potentially excessive force applied by the operator. An articulation lock allows the fixing and releasing of both neutral and articulated configurations of the tool and of consequent placement of the end effector.

40 Claims, 22 Drawing Sheets

(58) Field of Classification Search
USPC ..... 606/1; 600/137, 139, 142, 146, 150, 141
See application file for complete search history.

(56) References Cited

U.S. PATENT DOCUMENTS

| | | | |
|---|---|---|---|
| 3,071,161 A | 1/1963 | Ulrich | |
| 3,190,286 A | 6/1965 | Stokes | |
| 3,557,780 A | 1/1971 | Sato | |
| 3,605,725 A | 9/1971 | Bentov | |
| 4,466,649 A | 8/1984 | Ozawa | |
| 4,489,826 A | 12/1984 | Dubson | |
| 4,580,551 A | 4/1986 | Siegmund et al. | |
| 4,700,693 A | 10/1987 | Lia et al. | |
| 4,763,669 A | 8/1988 | Jaeger | |
| 4,790,294 A | 12/1988 | Allred et al. | |
| 4,834,761 A | 5/1989 | Walters | |
| 4,854,626 A | 8/1989 | Duke | |
| 4,880,015 A | 11/1989 | Nierman | |
| 4,984,951 A | 1/1991 | Jameson | |
| 5,174,276 A | 12/1992 | Crockard | |
| 5,174,300 A * | 12/1992 | Bales et al. | 600/564 |
| 5,257,618 A | 11/1993 | Kondo | |
| 5,271,381 A | 12/1993 | Ailinger et al. | |
| 5,273,026 A | 12/1993 | Wilk | |
| 5,286,228 A | 2/1994 | Lee et al. | |
| 5,297,443 A | 3/1994 | Wentz | |
| 5,314,424 A | 5/1994 | Nicholas | |
| 5,322,064 A | 6/1994 | Lundquist | |
| 5,325,845 A | 7/1994 | Adair | |
| 5,330,502 A | 7/1994 | Hassler et al. | |
| 5,354,162 A | 10/1994 | Burdea et al. | |
| 5,381,782 A | 1/1995 | DeLaRama et al. | |
| 5,403,342 A | 4/1995 | Tovey et al. | |
| 5,405,344 A | 4/1995 | Williamson et al. | |
| 5,425,743 A | 6/1995 | Nicholas | |
| 5,441,494 A | 8/1995 | Ortiz | |
| 5,454,827 A | 10/1995 | Aust et al. | |
| 5,476,479 A | 12/1995 | Green et al. | |
| 5,486,154 A | 1/1996 | Kelleher | |
| 5,490,819 A | 2/1996 | Nicholas et al. | |
| 5,498,256 A | 3/1996 | Furnish | |
| 5,513,827 A | 5/1996 | Michelson | |
| 5,520,678 A | 5/1996 | Heckele et al. | |
| 5,522,788 A | 6/1996 | Kuzmak | |
| 5,549,636 A | 8/1996 | Li | |
| 5,562,699 A | 10/1996 | Heimberger et al. | |
| 5,570,919 A | 11/1996 | Eusebe | |
| 5,599,151 A | 2/1997 | Daum et al. | |
| 5,609,601 A | 3/1997 | Kolesa et al. | |
| 5,620,415 A | 4/1997 | Lucey et al. | |
| 5,624,398 A | 4/1997 | Smith et al. | |
| 5,626,608 A | 5/1997 | Cuny et al. | |
| 5,632,432 A | 5/1997 | Schulze et al. | |
| 5,643,294 A | 7/1997 | Tovey et al. | |
| 5,647,743 A | 7/1997 | Schmitt | |
| 5,702,408 A | 12/1997 | Wales et al. | |
| 5,704,534 A | 1/1998 | Huitema et al. | |
| 5,713,505 A | 2/1998 | Huitema | |
| 5,716,352 A | 2/1998 | Viola et al. | |
| 5,759,151 A | 6/1998 | Sturges | |
| 5,792,164 A | 8/1998 | Lakatos et al. | |
| 5,807,376 A | 9/1998 | Viola et al. | |
| 5,813,813 A | 9/1998 | Daum et al. | |
| 5,823,066 A | 10/1998 | Huitema et al. | |
| 5,827,323 A * | 10/1998 | Klieman et al. | 606/205 |
| 5,836,960 A | 11/1998 | Kolesa et al. | |
| 5,845,540 A | 12/1998 | Rosheim | |
| 5,846,183 A | 12/1998 | Chilcoat | |
| 5,873,817 A | 2/1999 | Kokish et al. | |
| 5,899,425 A | 5/1999 | Corey et al. | |
| 5,916,146 A * | 6/1999 | Allotta et al. | 600/141 |
| 5,916,147 A | 6/1999 | Boury et al. | |
| 5,921,956 A | 7/1999 | Grinberg et al. | |
| 5,938,678 A | 8/1999 | Zirps et al. | |
| 5,947,984 A | 9/1999 | Whipple | |
| 5,961,532 A | 10/1999 | Finley et al. | |
| 6,019,722 A | 2/2000 | Spence et al. | |
| 6,050,996 A | 4/2000 | Schmaltz et al. | |
| 6,109,500 A * | 8/2000 | Alli | A61B 17/07207 227/175.2 |
| 6,161,543 A | 12/2000 | Cox et al. | |
| 6,250,532 B1 | 6/2001 | Green et al. | |
| 6,270,453 B1 | 8/2001 | Sakai | |
| 6,446,850 B2 | 9/2002 | Ming-Shun | |
| 6,464,704 B2 | 10/2002 | Schmaltz et al. | |
| 6,471,641 B2 | 10/2002 | Sakamoto | |
| 6,471,696 B1 | 10/2002 | Berube et al. | |
| 6,482,149 B1 | 11/2002 | Torii | |
| 6,491,626 B1 | 12/2002 | Stone et al. | |
| 6,571,042 B1 | 5/2003 | Kordahi | |
| 6,626,824 B2 | 9/2003 | Ruegg et al. | |
| 6,635,071 B2 | 10/2003 | Boche et al. | |
| 6,638,213 B2 | 10/2003 | Ogura et al. | |
| 6,638,287 B2 | 10/2003 | Danitz et al. | |
| RE38,335 E | 11/2003 | Aust et al. | |
| 6,641,528 B2 | 11/2003 | Torii | |
| 6,644,532 B2 | 11/2003 | Green et al. | |
| 6,666,854 B1 * | 12/2003 | Lange | 606/1 |
| 6,669,254 B2 | 12/2003 | Thom et al. | |
| 6,676,676 B2 | 1/2004 | Danitz et al. | |
| 6,682,541 B1 | 1/2004 | Gifford et al. | |
| 6,743,239 B1 | 6/2004 | Kuehn et al. | |
| 6,746,443 B1 | 6/2004 | Morley et al. | |
| 6,749,560 B1 | 6/2004 | Konstorum et al. | |
| 6,752,823 B2 | 6/2004 | Prestel | |
| 6,764,445 B2 | 7/2004 | Ramans et al. | |
| 6,773,327 B1 | 8/2004 | Felice et al. | |
| 6,817,972 B2 | 11/2004 | Snow | |
| 6,824,548 B2 | 11/2004 | Smith et al. | |
| 6,843,794 B2 | 1/2005 | Sixto, Jr. et al. | |
| 6,902,560 B1 | 6/2005 | Morley et al. | |
| 6,942,613 B2 | 9/2005 | Ewers et al. | |
| 6,945,979 B2 | 9/2005 | Kortenbach et al. | |
| 6,960,162 B2 | 11/2005 | Saadat et al. | |
| 6,960,163 B2 | 11/2005 | Ewers et al. | |
| 6,976,969 B2 | 12/2005 | Messerly | |
| 6,994,700 B2 | 2/2006 | Elkins et al. | |
| 7,138,976 B1 | 11/2006 | Bouzit et al. | |
| 7,480,600 B2 | 1/2009 | Massie et al. | |
| 7,553,275 B2 * | 6/2009 | Padget et al. | 600/142 |
| 2001/0023313 A1 | 9/2001 | Ide | |
| 2002/0096177 A1 | 7/2002 | Toti et al. | |
| 2002/0111604 A1 | 8/2002 | Doyle et al. | |
| 2002/0156497 A1 | 10/2002 | Nagase et al. | |
| 2002/0161281 A1 | 10/2002 | Jaffe et al. | |
| 2002/0177750 A1 | 11/2002 | Pilvisto | |
| 2003/0036748 A1 | 2/2003 | Cooper et al. | |
| 2003/0050649 A1 | 3/2003 | Brock et al. | |
| 2003/0078644 A1 | 4/2003 | Phan | |
| 2003/0109898 A1 | 6/2003 | Schwarz et al. | |
| 2003/0114838 A1 | 6/2003 | O'Neill et al. | |
| 2003/0135204 A1 | 7/2003 | Lee et al. | |
| 2003/0149338 A1 | 8/2003 | Francois et al. | |
| 2003/0153902 A1 | 8/2003 | Doyle et al. | |
| 2003/0229271 A1 | 12/2003 | Briscoe et al. | |
| 2003/0233026 A1 | 12/2003 | Saadat et al. | |
| 2004/0054322 A1 | 3/2004 | Vargas | |
| 2004/0138529 A1 | 7/2004 | Wiltshire et al. | |
| 2004/0138700 A1 | 7/2004 | Cooper et al. | |
| 2004/0236316 A1 * | 11/2004 | Danitz et al. | 606/1 |
| 2005/0090809 A1 | 4/2005 | Cooper et al. | |
| 2005/0096694 A1 * | 5/2005 | Lee | 606/205 |
| 2005/0107667 A1 | 5/2005 | Danitz et al. | |
| 2005/0119527 A1 | 6/2005 | Banik et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0009759 A1 | 1/2006 | Chrisitian et al. | |
| 2006/0020287 A1 * | 1/2006 | Lee et al. | 606/205 |
| 2006/0036255 A1 | 2/2006 | Pond et al. | |
| 2006/0058582 A1 | 3/2006 | Maahs et al. | |
| 2006/0094931 A1 | 5/2006 | Danitz et al. | |
| 2006/0111209 A1 | 5/2006 | Hinman et al. | |
| 2006/0111210 A1 | 5/2006 | Hinman | |

(56) References Cited

U.S. PATENT DOCUMENTS

| | | | |
|---|---|---|---|
| 2006/0111615 A1 | 5/2006 | Danitz et al. | |
| 2006/0111616 A1 | 5/2006 | Danitz | |
| 2006/0199999 A1 | 9/2006 | Ideda et al. | |
| 2006/0201130 A1 | 9/2006 | Danitz | |
| 2007/0276430 A1* | 11/2007 | Lee et al. | 606/205 |
| 2008/0065116 A1* | 3/2008 | Lee et al. | 606/142 |

FOREIGN PATENT DOCUMENTS

| | | |
|---|---|---|
| EP | 0 598 618 A2 | 5/1994 |
| EP | 0702937 A1 | 3/1996 |
| EP | 0 836 833 A2 | 4/1998 |
| EP | 1 132 041 | 9/2001 |
| EP | 1 395 398 B1 | 3/2004 |
| JP | H06197906 A | 7/1994 |
| JP | H06-262549 | 9/1994 |
| JP | 01-299768 | 10/2001 |
| WO | WO 01/10292 A1 | 2/2001 |
| WO | WO 02/13682 A1 | 2/2002 |
| WO | WO 2004/019769 A1 | 3/2004 |
| WO | WO 2004/105578 A3 | 12/2004 |
| WO | WO 2005/067785 A1 | 7/2005 |
| WO | WO 2005/120326 A3 | 12/2005 |
| WO | WO 2005/120327 A3 | 12/2005 |
| WO | WO 2006/057699 A1 | 6/2006 |
| WO | WO 2006/057700 A1 | 6/2006 |
| WO | WO 2006/057702 A2 | 6/2006 |
| WO | WO 2006/073581 A1 | 7/2006 |

OTHER PUBLICATIONS

Hinman, Cameron; U.S. Appl. No. 11/787,605 entitled "Tool with multi-state ratcheted end effector," filed Apr. 16, 2007.

Hinman et al; U.S. Appl. No. 11/787,599 entitled "Tool with end effector force limiter," filed Apr. 16, 2007.

Hegeman et al; U.S. Appl. No. 11/787,201 entitled "Articulating tool with improved tension member system" filed Apr. 16, 2007.

Danitz et al.; U.S. Appl. No. 12/109,333 entitled "Articulating instrument," filed Apr. 24, 2008.

Isbell Jr., Lewis; U.S. Appl. No. 12/542,589 entitled "Instrument with articulation lock," filed Aug. 17, 2009.

Hinman, Cameron; U.S. Appl. No. 12/508,478 entitled "Articulating mechanism," filed Jul. 23, 2009.

Hinman et al.; U.S. Appl. No. 12/725,377 entitled "Articulating mechanism with flex-hinged links," filed Mar. 16, 2010.

Danitz et al.; U.S. Appl. No. 12/766,818 entitled "Articulating instruments with joystick control," filed Apr. 23, 2010.

Danitz, David J.; U.S. Appl. No. 12/766,820 entitled "Articulating mechanism with bifurcating control," filed Apr. 23, 2010.

Danitz, David J.; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Hinman et al.; U.S. Appl. No. 12/816,359 entitled "Link systems and articulation mechanisms for remote manipulation of surgical or diagnostic tools," filed Jun. 15, 2010.

Cox, James; The minimally invasive Maze-III procedure; Operative Techniques in Thoracic and Cardiovascular Surgery; vol. 5; No. 1; pp. 79-92; Feb. 2000.

Simha et al.; The elctrocautery maze—how I do it; The Heart Surgery Forum; vol. 4; No. 4; pp. 340-345; Aug. 23, 2001.

Prasad et al.; Epicardial ablation on the beating heart: progress towards an off-pump maze procedure; The Heart Surgery Forum; vol. 5/ No. 2; pp. 100-104; Jun. 27, 2001.

Extended European Search Report for Application No. EP07812101, mailed on Feb. 4, 2014, 5 pages.

International Search Report and Written Opinion for Application No. PCT/US07/70914, mailed on Sep. 12, 2008, 5 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

TOOL WITH ROTATION LOCK

CROSS REFERENCE TO RELATED APPLICATIONS

This application claims priority under 35 U.S.C. §119 to U.S. Ser. No. 60/813,650 of Danitz and Hinman, entitled "Devices having locking rotation knobs and methods for using the same" and filed on Jun. 13, 2006 , the disclosure of which is incorporated herein by reference. This application is further related to the following concurrently filed US patent applications: "Tool with articulation lock" of Hegeman, Danitz, Hinman, and Alvord, U.S. application Ser. No. 11/787,543 filed Apr. 16, 2007, "Tool with end effector force limiter" of Hinman and Bertsch, U.S. application Ser. No. 11/787,599 filed Apr. 16, 2007, "Tool with multi-state ratcheted end effector" of Hinman, U.S. application Ser. No. 11/787,605 filed Apr. 16, 2007, and "Articulating tool with improved tension member system" of Hegeman, Danitz, Bertsch, Hinman, and Alvord, U.S. application Ser. No. 11/787,608 filed Apr. 16, 2007.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates to articulating mechanisms and applications thereof, including the remote guidance and manipulation of surgical or diagnostic instruments tools.

BACKGROUND OF THE INVENTION

The popularity of minimally invasive surgery has been growing rapidly due to its association with decreased complication rates and post-surgical recovery times. The instruments employed are generally hand-operable and typically include a handle, a shaft that may or may not be rotatably attached to the handle, a rotation knob rigidly fixed to the proximal end of the shaft near the handle in instances where the shaft is rotatably attached to the handle, and a tool or end effector attached to the distal end of the shaft. To manipulate the instruments, they are held at the handle and typically pivoted about a pivot point defined by the entry incision, i.e., the incision made in the abdominal wall for laparoscopic procedures. The end effector may also be rotated about the shaft axis, as for example, by rotating a rotation knob, if present. In use, these instruments have limited control and range of motion and become physically taxing as the length of the procedure increases.

Surgical procedures such as endoscopy and laparoscopy typically employ instruments that are steered within or towards a target organ or tissue from a position outside the body. Examples of endoscopic procedures include sigmoidoscopy, colonoscopy, esophagogastroduo-denoscopy, and bronchoscopy, as well as newer procedures in natural orifice transluminal endoscopic surgery ("NOTES"). Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Recently, surgical instruments, including minimally invasive surgical instruments, have been developed that are more ergonomic and which have a wider range of motion and more precise control of movement. These instruments may include mechanisms that articulate using a series of links coupled with one or more sets of tension bearing members, such as cable. As with conventional instruments used in minimally invasive surgery, rotation of the shaft and end effector with respect to the handle is an important feature of cable and link type instruments to aid with dissecting, suturing, retracting, knot tying, etc. Ergonomic, flexible, and intuitive mechanisms that facilitate manual control of the end effectors of such instruments are also important factors as medical procedures become more advanced, and as surgeons become more sophisticated in operating abilities. Particularly with regard to rotation, however, inadvertent rotation and larger torques can be associated with articulating instruments, as loading on the end effector that can be off axis from the shaft axis. Consequently, new mechanisms and methods for controlling rotation of surgical instruments are desirable.

SUMMARY OF THE INVENTION

It may at times be desirable to change and then maintain the orientation of the distal end of a steerable or articulating instrument. This invention provides methods and devices for rotating, articulating, locking or otherwise maintaining the shape and orientation of steerable and articulating instruments.

Embodiments of the inventive device include proximal portion and a distal portion, a shaft interposed between the proximal portion and the distal portion. The shaft includes an articulation mechanism for manipulating the angular orientation of the end effector with respect to the shaft, and a shaft rotation mechanism which permits rotation of the articulation mechanism and the distal portion with respect to the handle. The rotation mechanism has a first state in which the articulation mechanism and distal portion are not rotatable with respect to the handle and a second state in which the articulation mechanism and distal portion are rotatable with respect to the handle. Some embodiments of the device may be a surgical or diagnostic tool, and some embodiments may include an end effector disposed at the distal portion of the device.

Some embodiments of a shaft rotation mechanism include a handle engagement surface that is engaged with the handle in the first state, thus preventing rotation, and is not engaged with the handle in the second state, thereby permitting rotation. In some embodiments, the handle engagement surface includes a plurality of teeth and the handle also includes a complementary plurality of teeth that are adapted to engage the teeth of the handle engagement surface, when the shaft rotation mechanism is in its first state, such that rotation is not allowed. In some embodiments, the handle includes a movable lock actuator that supports the plurality of teeth on the handle.

In some embodiments, the shaft rotation mechanism is biased toward this first and non-rotatable state. In some embodiments this bias includes a spring, which biases the shaft rotation mechanism toward the non-rotatable state.

Some embodiments of the shaft rotation mechanism include a shaft engagement mechanism that is engaged with the articulation mechanism in both the first and second states of the rotation mechanism. This shaft engagement mechanism may be movable proximally and distally along the shaft between the first (non-rotatable) state and the second (rotatable) state. The shaft rotation mechanism may further include a shaft rotation actuator that engages with the articulation mechanism such that the rotation of the shaft rotation actuator rotates the articulation mechanism and the distal portion of the device with respect to the handle. In such embodiments, the shaft rotation actuator cannot rotate with respect to the handle when the shaft rotation mechanism is in the first state.

In some embodiments of the tool, the articulation mechanism includes a pair of a proximal link and a distal link spaced apart from each other, and configured such that movement of the proximal link causes corresponding relative movement of the distal link and angular movement of the distal portion of the tool, and, if present, the end effector with respect to the shaft. In some embodiments, rather than a single distal and proximal pair of links, the tool includes a plurality of pairs of proximal and distal links, such that movement of the proximal link of each pair causes corresponding relative movement of the distal link of the pair and angular movement of the end effector with respect to the shaft. In some embodiments, the shaft rotation mechanism includes a sliding engagement with a proximal link. In some embodiments the articulation mechanism further includes an articulation lock having an engaged position and a disengaged position, such that when in the engaged position, the articulation lock impedes relative movement of the proximal links of each pair of links, thereby preventing relative movement of the distal link of each pair of links.

Embodiments of the invention include a method of using a device, the device as summarized above, where the method of use includes placing the distal portion of the device and the end effector, if present at the distal portion, at a target site, moving the handle of the tool angularly with respect to the shaft and thereby moving the distal portion angularly with respect to the shaft, rotating the handle with respect to the shaft without rotating distal portion, and applying rotational torque to the distal portion by rotating the handle.

The step of rotating the handle with respect to the shaft may include moving a shaft rotation actuator from a first position to a second position. The method may further include moving the shaft rotation actuator from the second position to the first position prior to the step of applying rotational torque to the distal portion of the device and the end effector, if present. In some embodiments the first position is proximal to the second position.

The step of rotating the handle with respect to the shaft may include rotating the handle with respect to the shaft rotation actuator. Rotating the handle may include rotating the handle with respect to the shaft rotation actuator while the shaft rotation actuator is in the second position.

The method of using a device such as an articulatable surgical or diagnostic tool, as summarized above, may further include controlling permissibility of relative angular movement between the handle and the shaft. The step of controlling permissibility may include impeding angular movement by moving an articulation lock from a disengaged position to an engaged position, wherein in the engaged position the articulation lock impedes movement of the proximal link and corresponding relative movement of the distal link. The articulation lock may include a slidable sleeve, and moving the lock may include sliding the sleeve along the shaft, and moving the sleeve along the shaft may be in a proximal direction. The step of controlling permissibility may include permitting angular movement by moving the articulation lock from the engaged position back to the disengaged position to permit relative angular movement between the handle and the shaft.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings which are briefly described below.

FIG. 21A shows a rotated front view, FIG. 21B shows a rotated end view, and FIG. 21C shows a top front view.

DETAILED DESCRIPTION OF THE INVENTION

Steerable articulating instruments are described in U.S. Pat. No. 7,090,637; US 2005/0107667; US Publication Nos. US 2005/0273084; US 2005/0273085; US 2006/0111209, and US 2006/0111210. The articulating mechanisms of the tools described in those publications use multiple pairs of segments or links that are controlled, e.g., by multiple sets of cables. Depending upon the specific design of the device, the links can be discrete segments (as described, e.g., in U.S. Pat. No. 7,090,637) or discrete portions of a flexible segment (as described, e.g., in US 2005/0173085). The instrument may also include steerable or controllable links separated by spacer links, e.g., as described in US 2005/0273084 and US 2006/0111210.

When using such articulating instruments, a user may manipulate the proximal end of the instrument, and thereby move one or more proximal links of the articulation mechanism. This movement results in relative movement of the distal link(s) corresponding to the proximal link(s). It may at times be desirable to lock or otherwise maintain the straight or bent shape of the instrument. In certain embodiments of this invention, the shape of the instrument is maintained by preventing movement of at least one of the proximal links with respect to the rest of the instrument. In other embodiments, a friction-based articulation locking mechanism locks all links, proximal and distal; these embodiments are disclosed in the concurrently filed and hereby incorporated application "Tool with articulation lock" of Hegeman, Danitz, and Alvord.

FIGS. 1-6 show an articulatable tool 100 with an end effector 102 at its distal end and an end effector actuator 104 within a handle 106 at its proximal end. Instrument 100 may be used, e.g., in a laparoscopic procedure requiring grasping or cutting within a patient. Exemplary embodiments of the tool 100 may also may useful in endoscopic procedures, particularly when, as in some embodiments, the tool has a flexible shaft. Still other embodiments may be used for percutaneous procedures, such as a catheter. Still other embodiments include devices that are directed toward natural orifice transluminal endoscopic surgery ("NOTES"). Embodiments of the invention may include a wide variety of tools, some with medical or diagnostic purposes, and others that are applied to other types of tasks where the articulational capabilities of the tool provide benefit.

Figure 3:
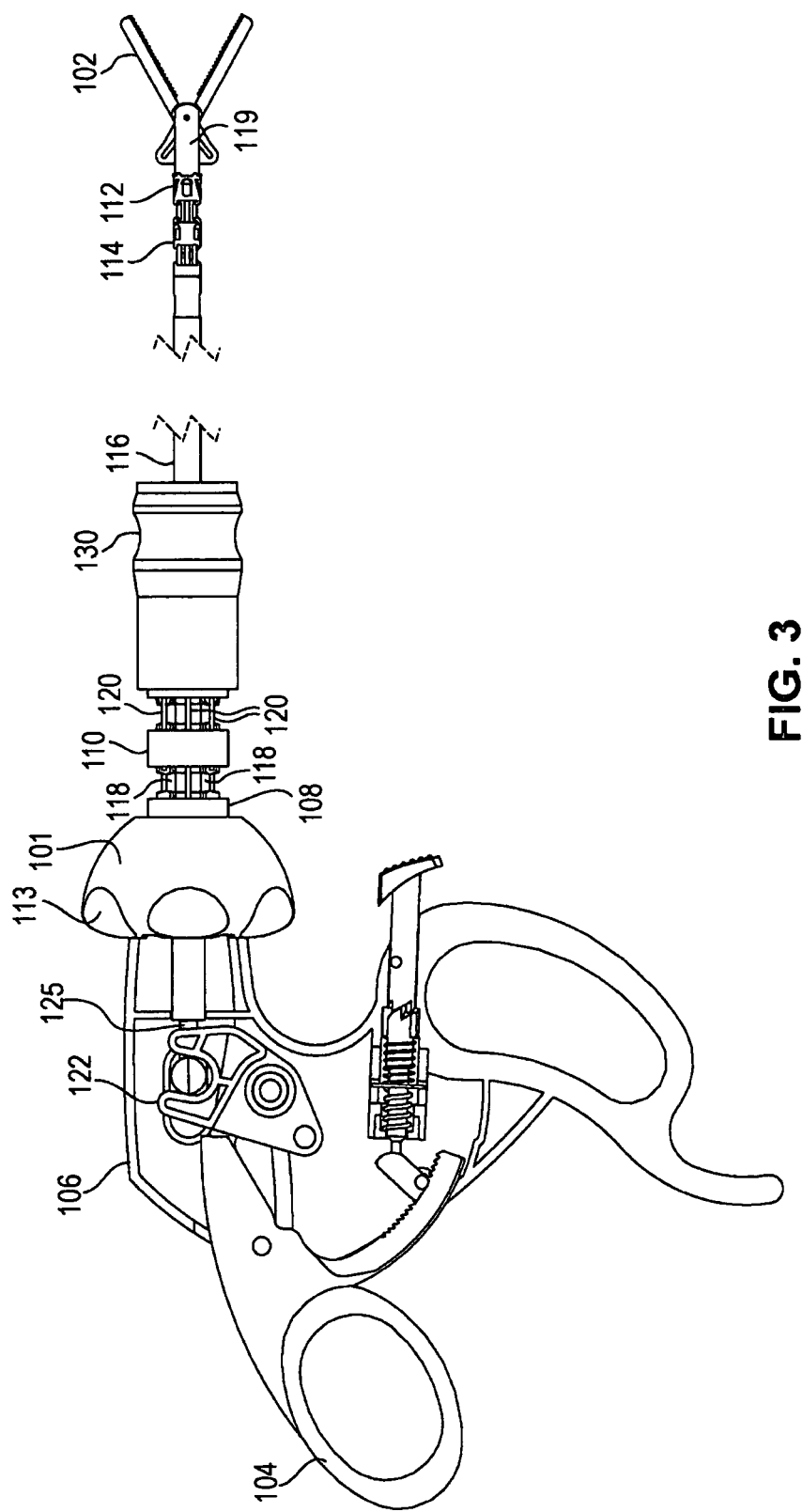
FIG. 3 is an exposed side view of a surgical tool with an end effector actuator and an end effector both in an open position.
Figure 8:
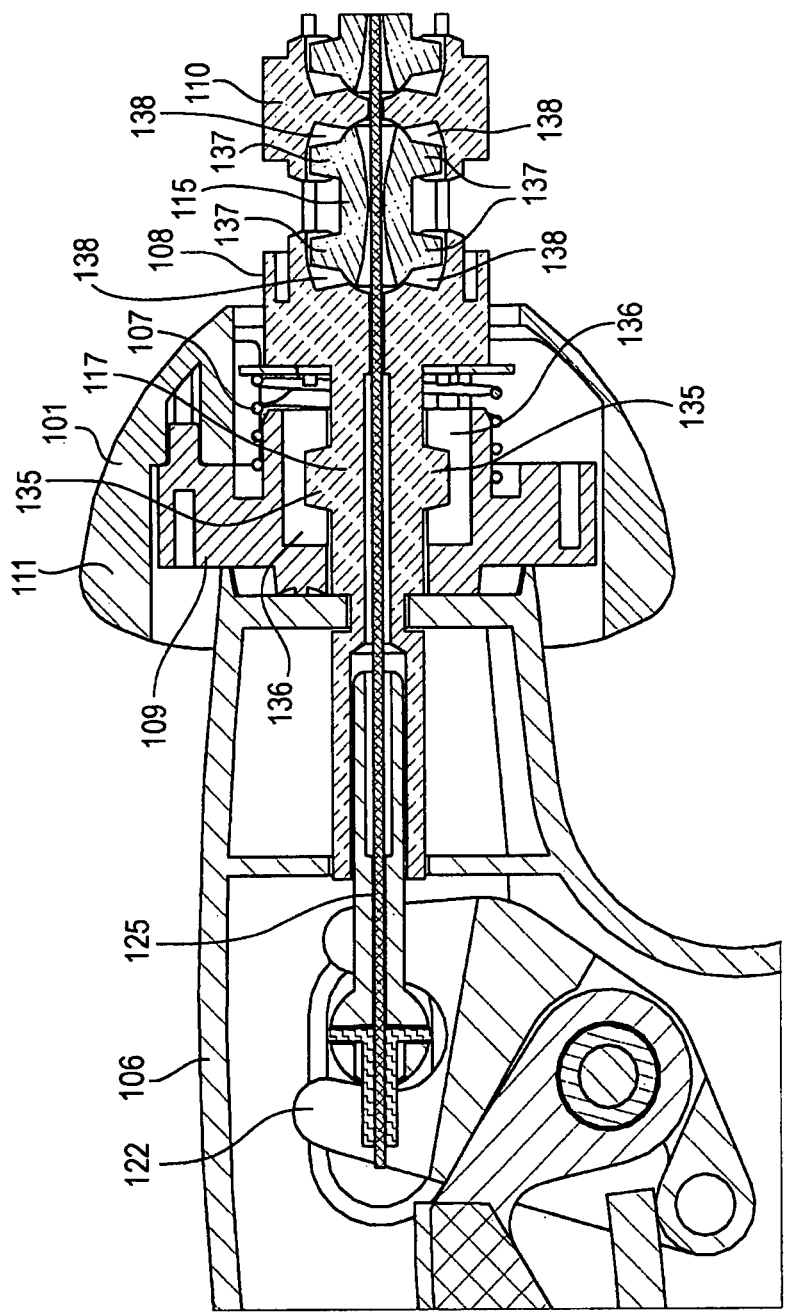
FIG. 8 is a cross-sectional view of a portion of the handle, knob and a proximal link.
Figure 26:
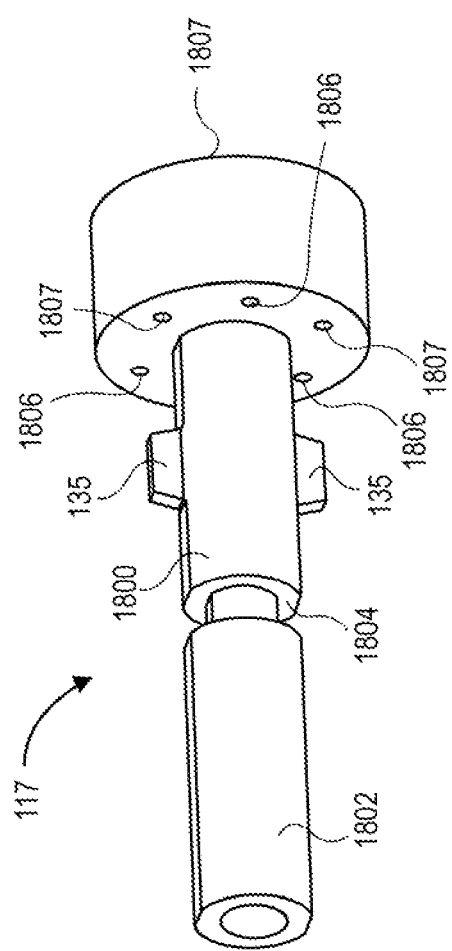
FIG. 26 is a distal-looking perspective view of a spindle having a proximal link formed on its distal end.
Figure 27:
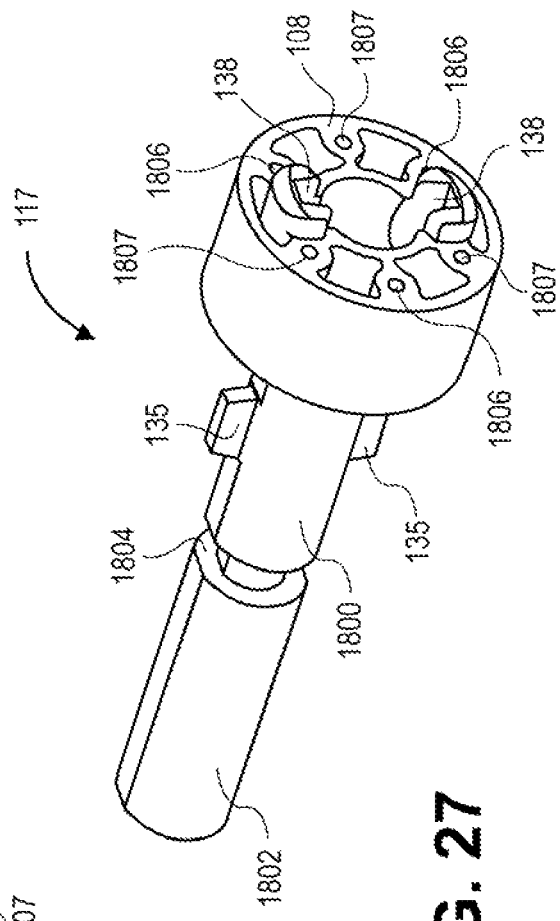
FIG. 27 is a proximal-looking perspective view of a spindle having a proximal link formed on its distal end.

Continuing now with some description of links that typically form the basis of articulating mechanisms included with some embodiments of the tools with rotatable mechanisms, links may be understood as a discrete portion of a tool that are capable of movement with respect to an adjacent portion. Links typically occur in complementary or corresponding pairs, one link being proximal on the tool, the other link being distal, the two links being operably connected, typically by tension bearing members such as cables. Proximal articulation links 108 and 110 extend distally from handle 106, and complementary distal articulation links 112 and 114 extend proximally from end effector 102. Proximal link 108 is connected to and moves with handle 106. In the embodiment shown, proximal link 108 is formed on the distal end of spindle 117 which is rotatably held in handle 106, as best seen in FIGS. 8, 26, and 27. Likewise, complementary distal link 112 is connected to and moves with end effector 102. Distal link 112 may be integrally formed on the proximal end of end effector body 119, as best seen in FIG. 3. An elongated shaft 116 is disposed between complementary pairs of links proximal and distal to it. In the tool embodiment shown in FIG. 8, a bushing 115 separates links 110 and 112. Bushing 115 has convex surfaces at its proximal and distal ends that engage with corresponding concave surfaces on links 108 and 110. Further details of the types links suitable for use with this invention, such as ball and socket joints, and pivoting single-degree-of freedom joints, or any type of joint where friction affects the movement of links relative to each other, may be found in US 2005/0273084 US 2006/0111209, and US 2006/0111210.

As seen in FIG. 3, a set of tension bearing members or control cables 118 is attached to proximal link 108, extends through proximal link 110, shaft 116, and distal link 114, and is attached to distal link 112. A second set of control cables 120 is attached to proximal link 110, extends through shaft 116 and is attached to distal link 114. In this embodiment, there are three control cables 118 in the first set and three control cables 120 in the second set. It should be appreciated, however, that other numbers of control cables may be used to connect corresponding proximal and distal links. In addition, mechanisms other than cables may be used to connect corresponding links.

Figure 2:
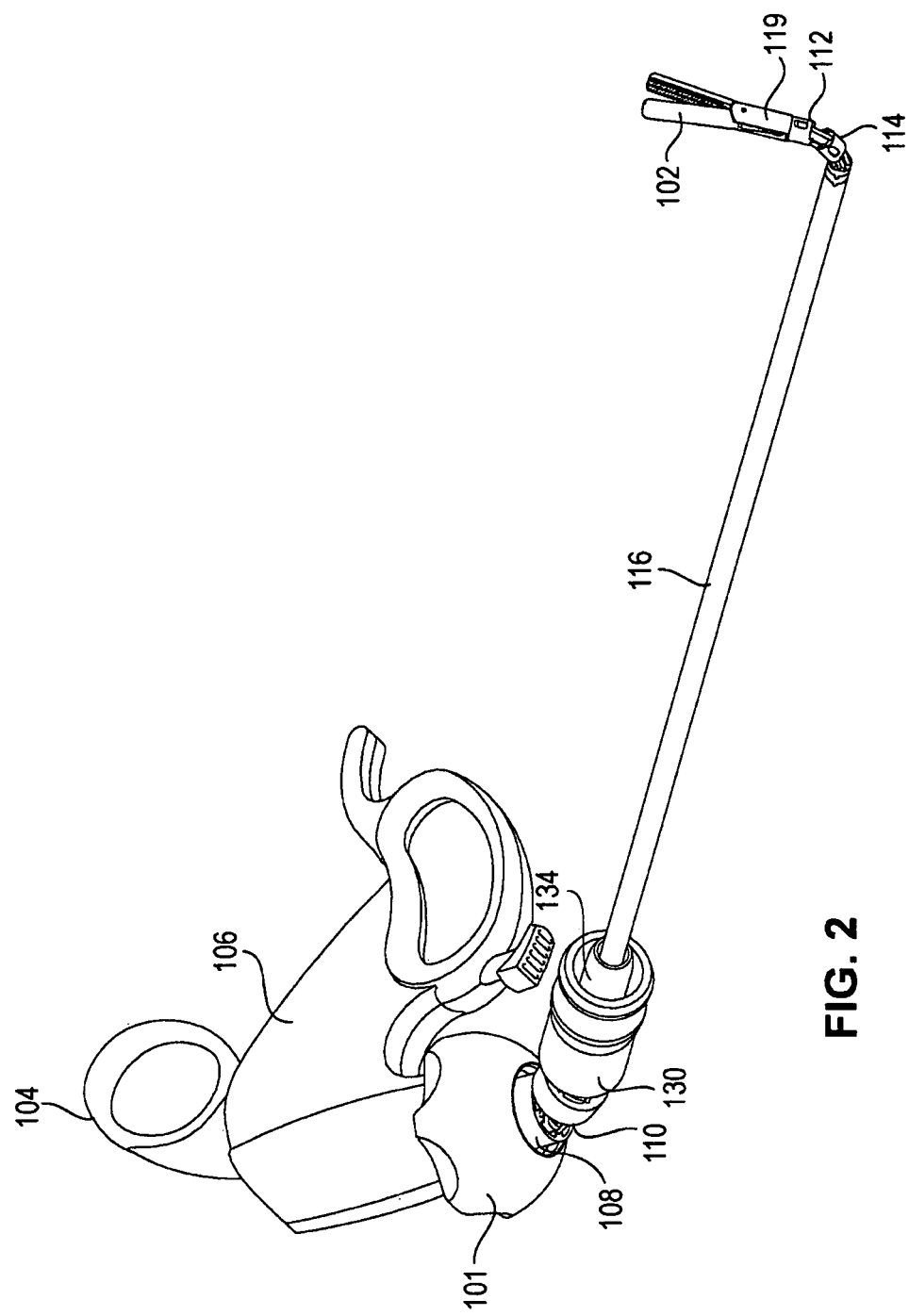
FIG. 2 is perspective view of a surgical tool in an articulated position.

As shown in FIG. 2, which shows a tool in an articulated position, movement of handle 106 and proximal link 108 with respect to proximal link 110 moves end effector 102 and distal link 112 in a relative and corresponding manner. Likewise, movement of proximal link 110 with respect to shaft 116 moves distal link 114 with respect to shaft link 116 in a relative and corresponding manner, also as shown in FIG. 2. This relative articulation movement provides a way for a user to remotely manipulate the end effector through movement of the handle. Angular movement of the end effector may either mirror the movement of the handle or be reciprocal to it; FIG. 2 shows the end effector moving in a manner that mirrors the movement of the handle.

Figure 4:
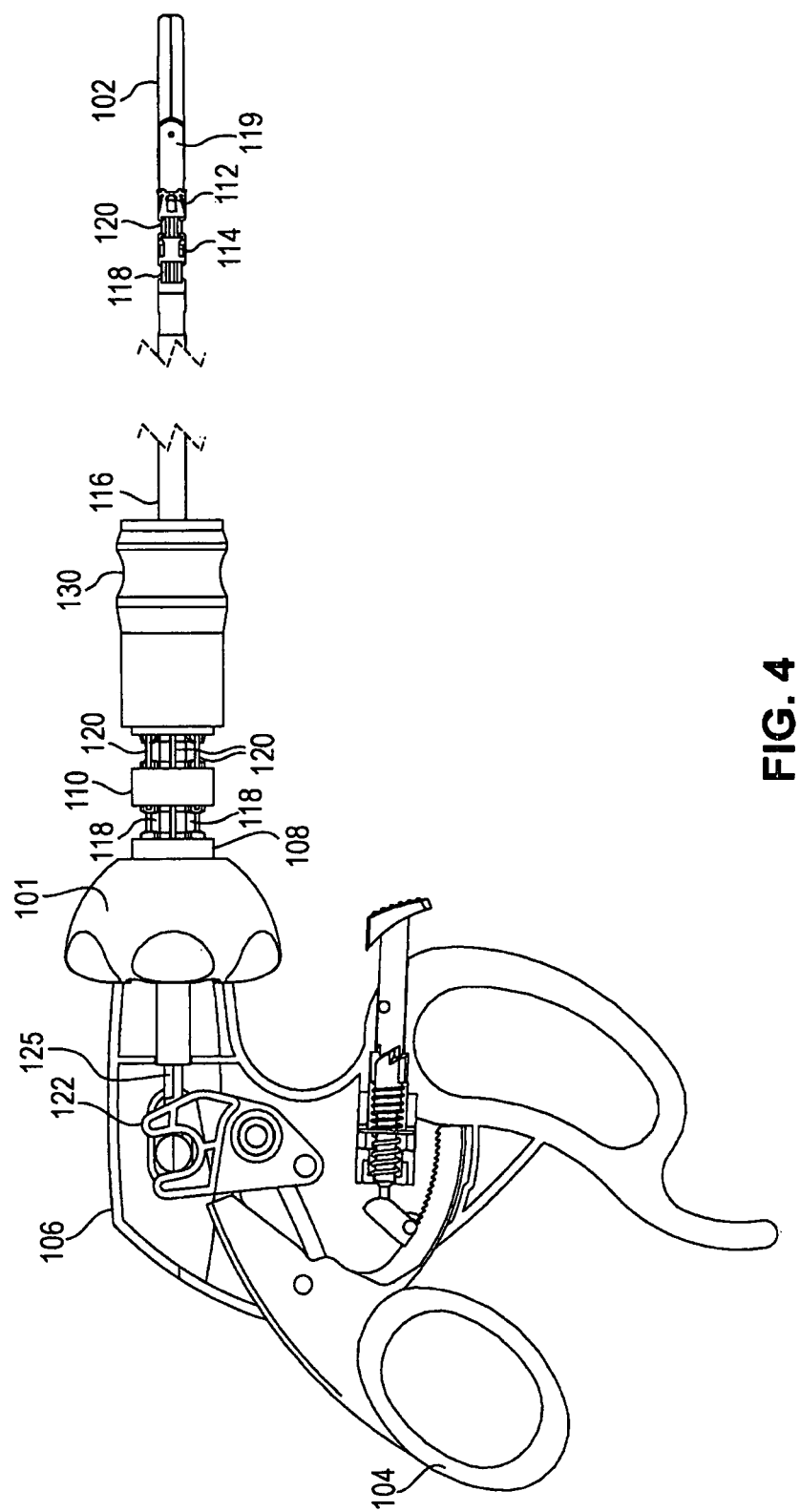
FIG. 4 is an exposed side view of a surgical tool with an end effector actuator and an end effector both in a closed position.
Figure 5:
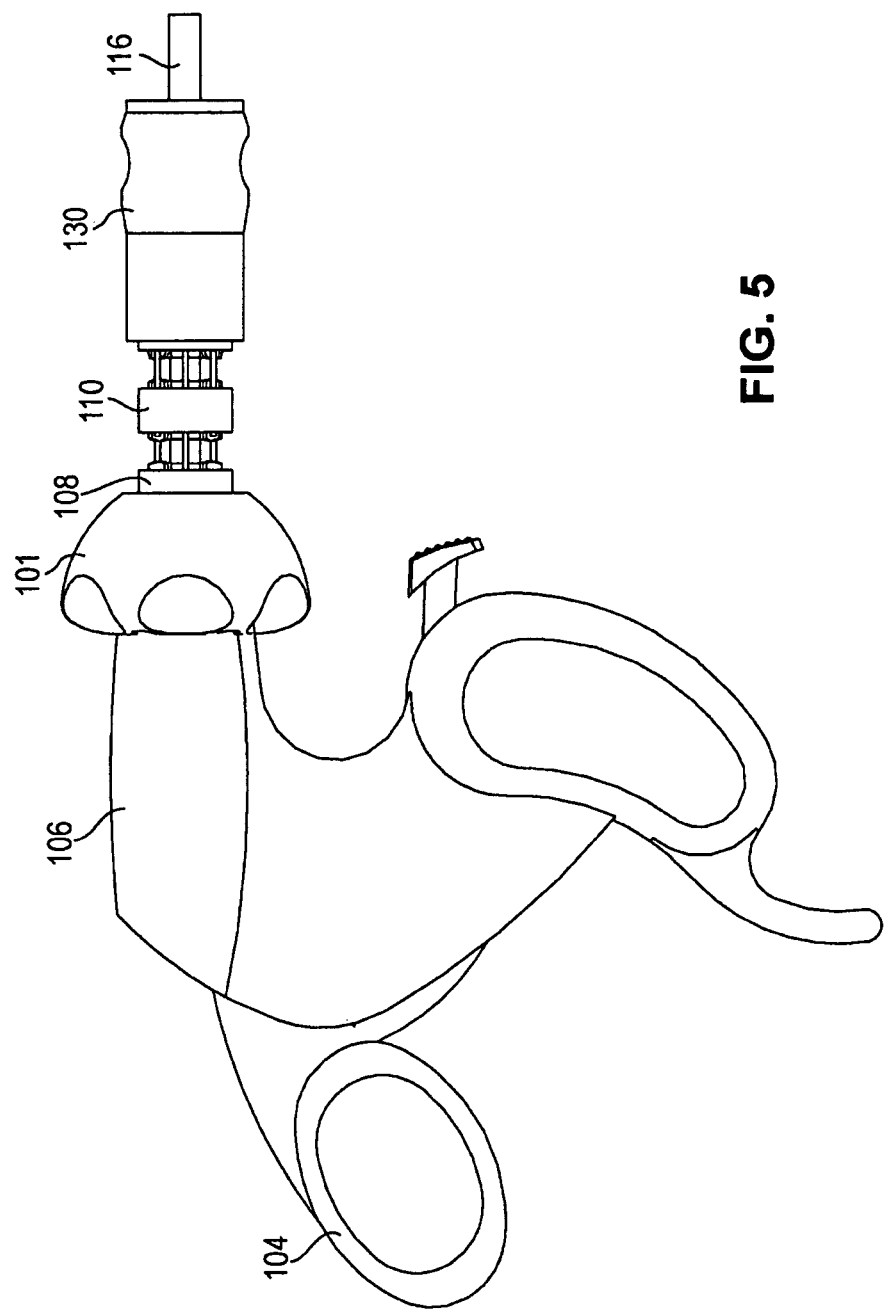
FIG. 5 is a side view of the proximal portion of a tool, showing the handle and proximal end of the shaft, with an articulation locking sleeve in a distal and unlocked position.

In the embodiment illustrated in FIGS. 1-4, the end effector 102 is a pair of jaws. Actuation force is transmitted from end effector actuator 104 through a transmission that includes a linearly movable tension bearing member or rod 125 and a rotatable rod actuator 122, as shown in FIGS. 3 and 4. In some embodiments, rod 125, in addition to being a tension bearing member, is further able to function as a compression bearing member such that it can transfer a compressive load from the end effector actuator distally to the end effector. The depicted embodiment of the end effector actuator 104 may be referred to, for example, as a moveable member, or a thumb piece, as it is typically operated by the thumb of a user. Other embodiments of end effectors (surgical, diagnostic, etc.) and end effector actuators may be used with the articulating tool of this invention.

Turning now to description of mechanisms that reversibly prevent or permit articulation in articulating tools in order to maintain a particular position of the end effector with respect to the shaft (whether the position is a straight or neutral position, or an articulated position) the articulating tool of this invention may include an articulation lock. The articulation lock embodiment in the form of a rigid sleeve described below is merely one example. As noted above, numerous other embodiments are provided in the concurrently filed application of Hegemen et al., entitled "Tool with Articulation Lock", which is hereby incorporated into this application by this reference.

Thus, by way of an articulation lock example, the embodiment of an articulation lock shown in FIGS. 1-6 includes a movable rigid sleeve 130. In the unlocked position, as shown in FIGS. 1-5, sleeve 130 is distal to proximal links 108 and 110, and they are thus exposed to view. In the locked position shown in FIG. 6, however, sleeve 130 has been moved proximally to a position adjacent to and covering links 108 and 110 as well as the proximal end of shaft 116 which, accordingly, are hidden in this view. The movable sleeve, in this position, thereby physically blocks relative movement between links 108 and 110 and between link 110 and shaft 116. In this locked position, relative movement between distal links 112 and 114 and between link 114 and shaft 116 is prevented as well.

Figure 6:
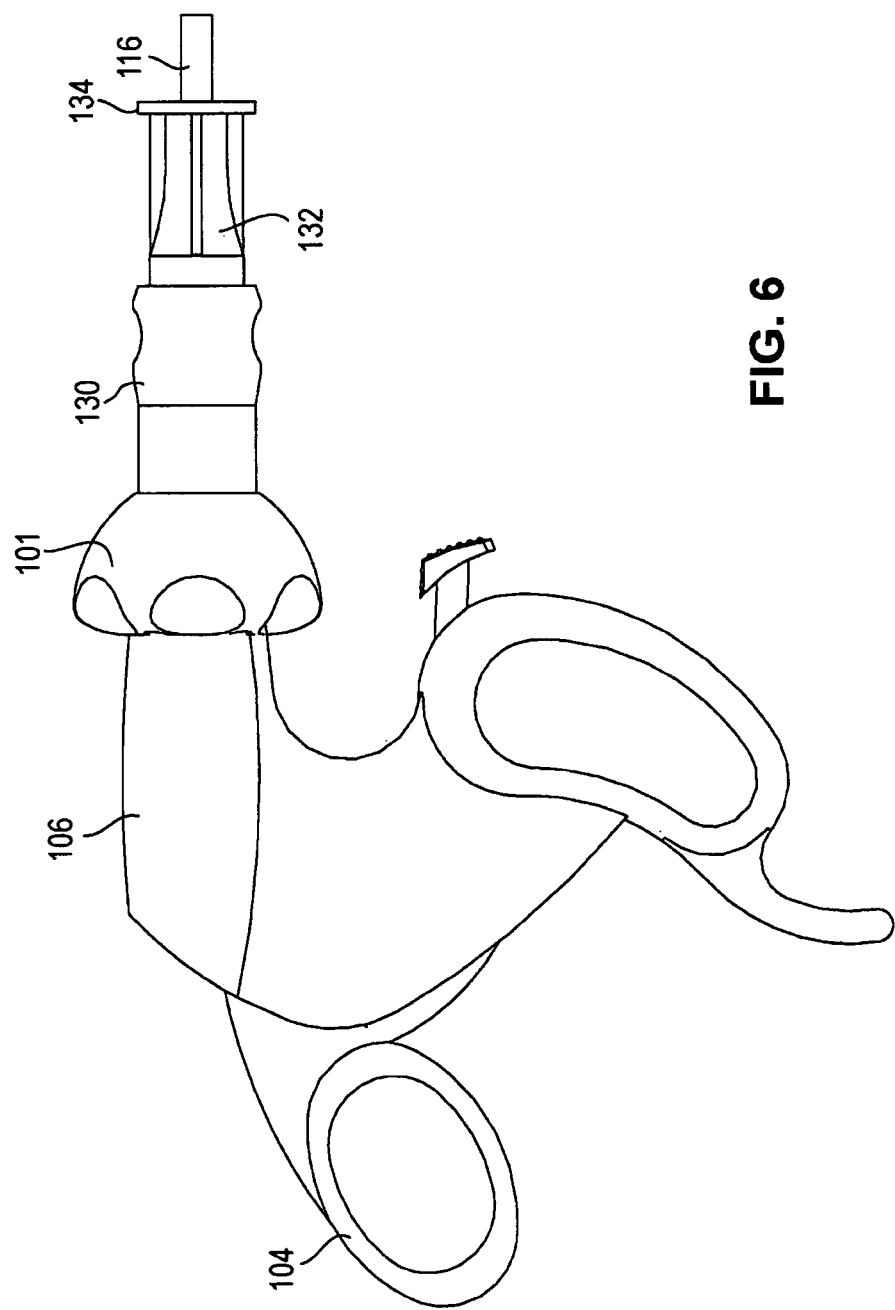
FIG. 6 is a side view of the proximal portion of a tool, showing the handle and proximal end of the shaft, with an articulation locking sleeve in a proximal and locked position.
Figure 7:
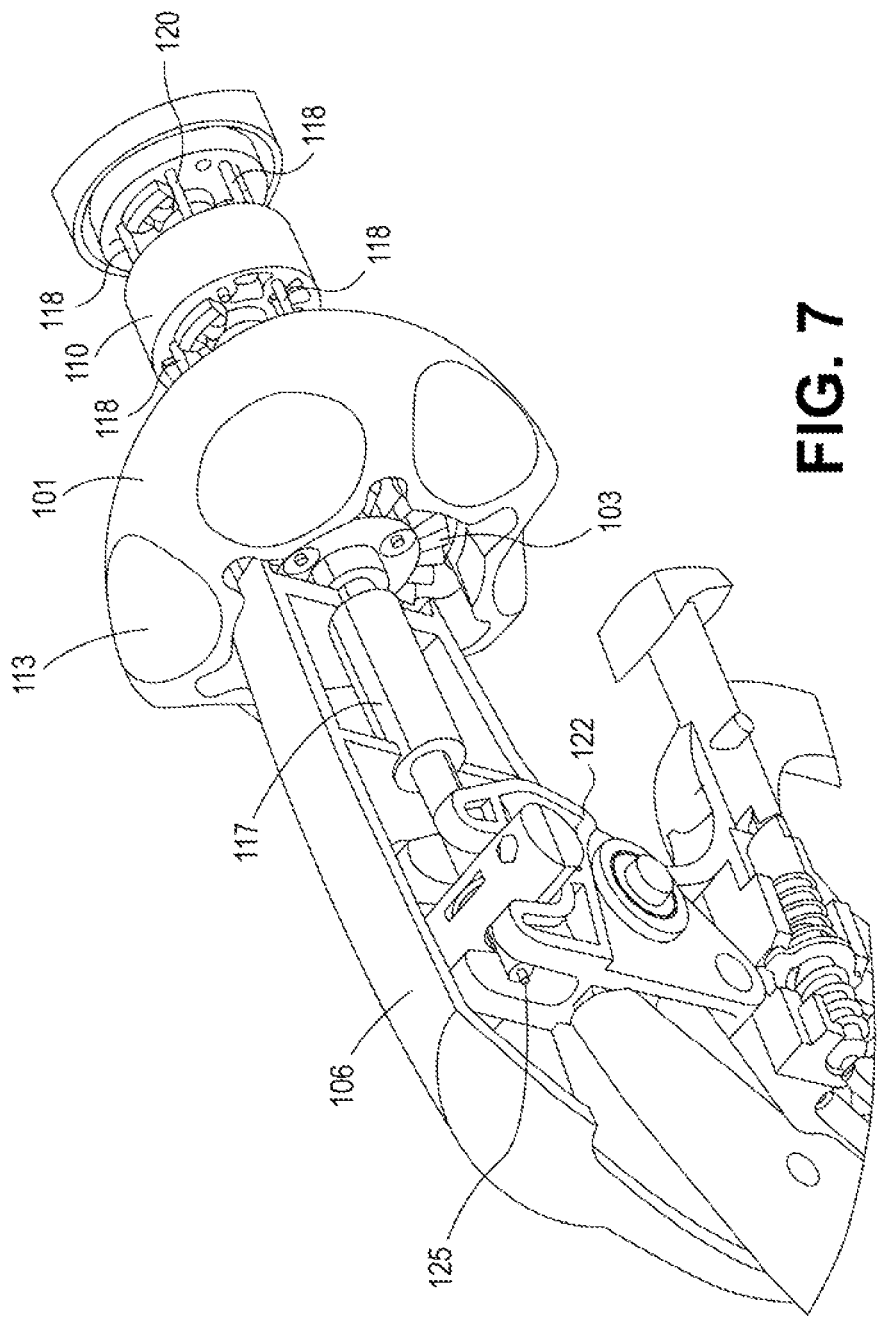
FIG. 7 is an exposed view of a portion of a tool from an overhead distal looking perspective, the portion including the handle, locking rotation knob, and a proximal link.

As shown in FIG. 6, a sleeve support mechanism 132 extends proximally from shaft 116 to provide sliding support for sleeve 130. A distal stop 134 provides a limit of distal movement of sleeve 130; a similar stop (not shown) is provided on or within handle 104 to limit proximal movement of sleeve 130. Detents, ridges or other mechanisms may be provided to maintain the sleeve in its proximal or distal positions and to provide tactile feedback to the user regarding the position of the sleeve.

Figure 10:
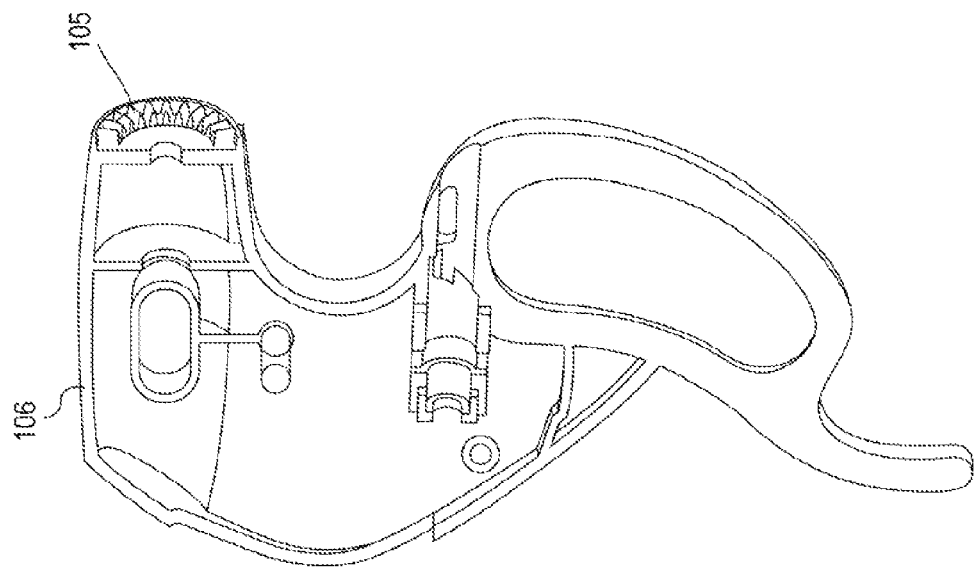
FIG. 10 is an exposed view of a handle from a proximal-looking perspective.
Figure 9:
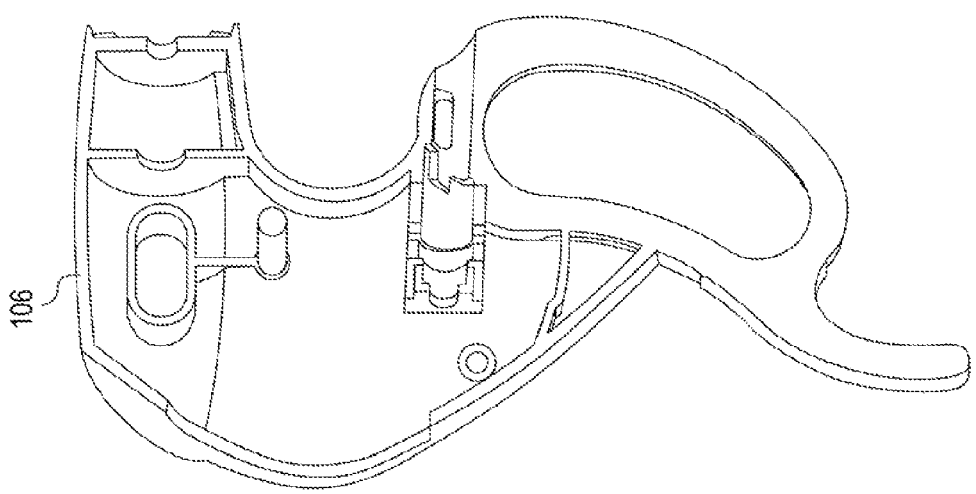
FIG. 9 is an exposed view of a handle from a distal-looking perspective.
Figure 12:
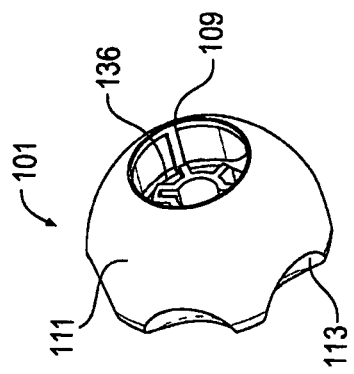
FIG. 12 is a proximal-looking perspective view of a locking rotation knob with inner and outer members fitted together.
Figure 14:
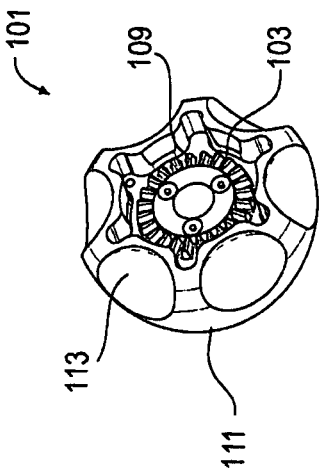
FIG. 14 is a distal-looking perspective view of a locking rotation knob showing an inner member and an outer member fitted together.

Turning now to embodiments of an inventive rotation lock, the end effector 102 of tool 100 may be rotated with respect to handle 106 and then locked so that further rotation between end effector 102 and handle 106 is prevented. A rotation knob 101 is disposed at least partially around link 108. In the locked position, teeth 103 formed on the proximal face of knob 101 engage corresponding teeth 105 formed on a distal face of handle 106, as seen in FIG. 10. (Handle 106 may be made in two pieces. Two views of one of the two pieces are shown in FIGS. 9 and 10.) In this embodiment, the rotation lock is self-locking due to the action of a spring 107 biasing knob 101 proximally into engagement with handle 106, as shown in FIG. 8.

Figure 11:
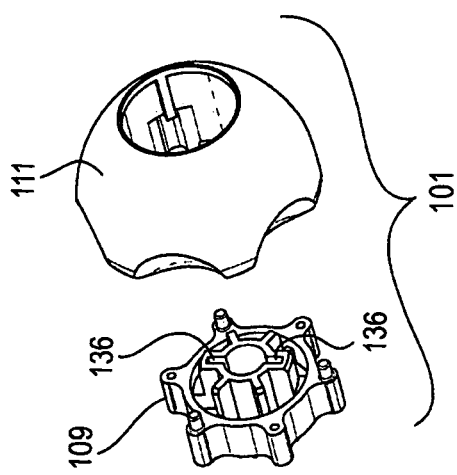
FIG. 11 is a proximal-looking perspective view of a locking rotation knob showing an inner member and an outer member separated from each other.
Figure 13:
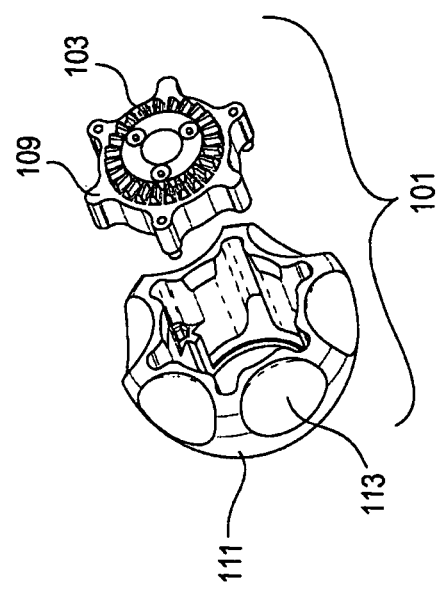
FIG. 13 is a distal-looking perspective view of a locking rotation knob showing an inner member and an outer member separated from each other.

When moved distally against the bias of spring 107, the teeth 103 of knob 101 disengage from the teeth 105 of handle 106. This disengagement permits knob 101, links 108 and 110, shaft 116, links 112 and 114, and end effector 102 to rotate with respect to handle 106. This relative rotation may be effected by rotating handle 106 while the rest of tool 100 remains stationary, by holding handle 106 stationary and rotating the rest of tool 100 such as by turning knob 101, or by a combination of the two. This action permits the end effector to be rotated in any articulated configuration. When end effector 102 is rotated in this fashion, it rotates about its own central axis. When the end effector has been rotated the desired amount relative to handle 106 by rotating knob 101 and/or handle 106, release of knob 101 permits the two sets of teeth to re-engage, thereby locking the device against further rotation. In the embodiment shown, spindle 117 is rotatably fixed relative to knob 101 by fins 135 formed on spindle 117 (as best seen in FIGS. 26 and 27) which are slidably received within slots 136 formed in inner member 109 of knob 101 (as best seen in FIG. 11). Bushing 115, in turn, may be rotatably fixed relative to spindle 117 by a torque transmitting pin or flanges 137 of bushing 115 (as best seen in FIG. 8) engaging slots 138 of proximal link 108 on spindle 117 (as best seen in FIG. 27). Similar torque-transmitting features may be provided along tool 100 between bushing 115 and end effector 102, as described in detail in U.S. application publication number US 2006/0111210. With this arrangement, the rotational orientation of end effector 102 relative to handle 106 may be locked when teeth 103 of knob 101 engage teeth 105 of handle 106, as described above.

In one embodiment, knob 101 is made in two pieces, an inner member 109 and an outer member 111, as shown in FIGS. 11-14. The teeth 103 are formed on the inner member 109. Indentations or knurls 113 may be formed on knob 101 to facilitate grasping.

Figure 1:
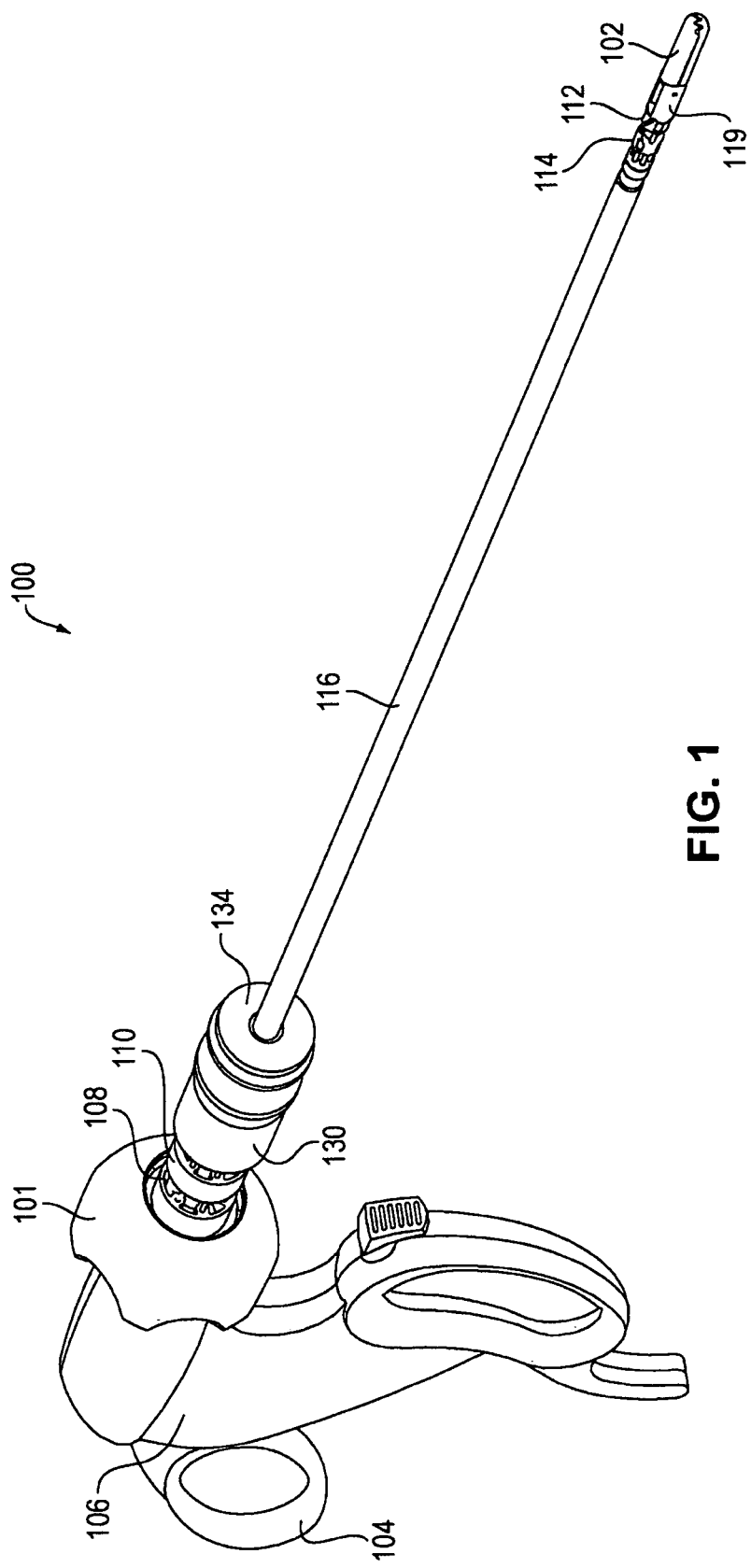
FIG. 1 is a front perspective view of a surgical tool.

In other embodiments, the rotation knob may not be self-locking in the sense that the locking mechanism is not biased toward a locked position, and may have a manually actuatable lock, such as a sliding lock. In some embodiments, the engagement surfaces between the rotation knob and the handle may use fewer locking teeth or other engagement features, such as pins, friction surfaces, etc. While the end effector shown in FIG. 1 is a pair of jaws, other end effectors may be used, such as meters, probes, retractors, dissectors, staplers, clamps, graspers, scissors, cutters, ablation elements, etc.

Figure 15:
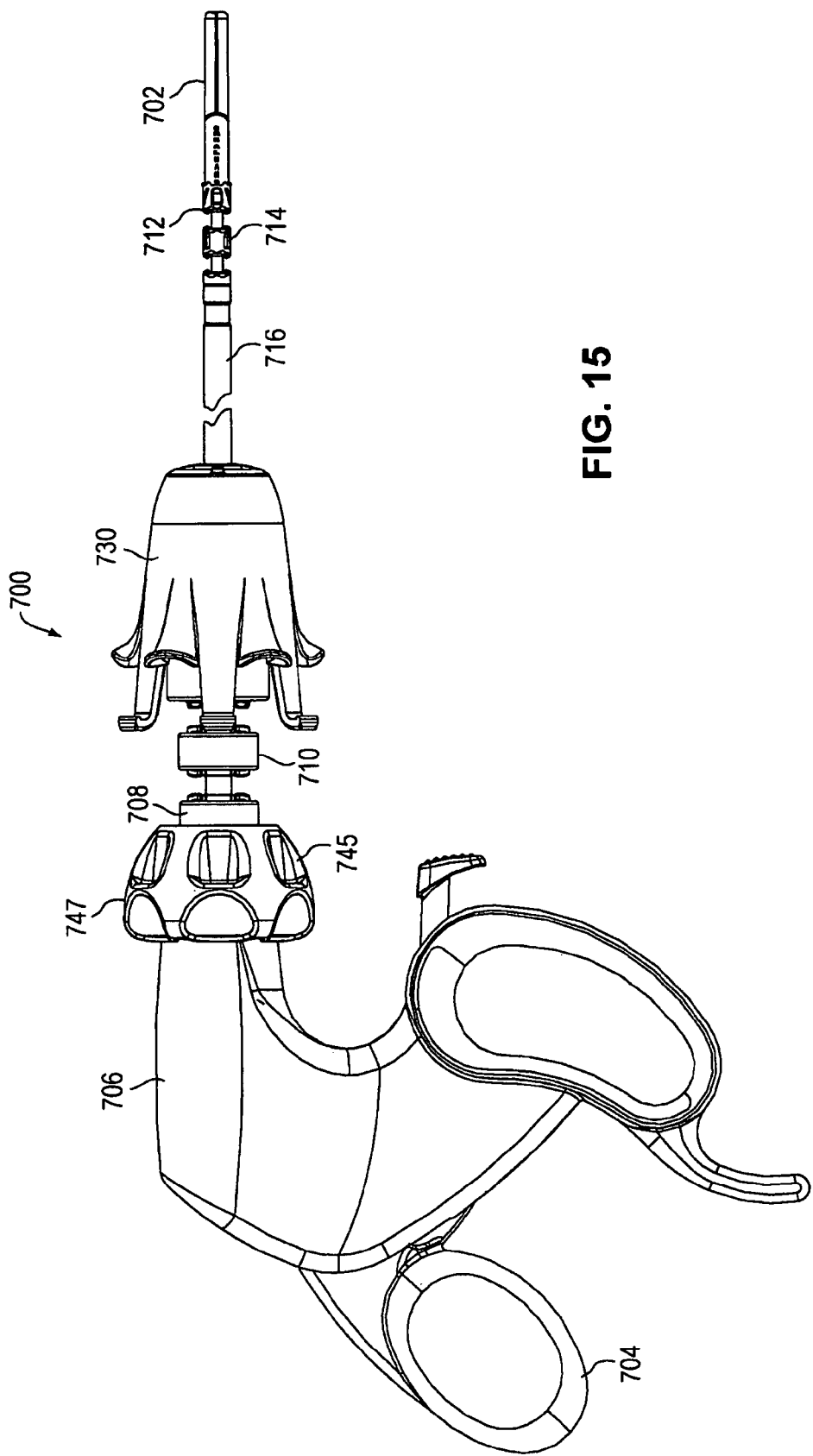
FIG. 15 is a side view of another embodiment of surgical tool, with a different embodiment of an articulation locking sleeve in a distal and unlocked position, and with an end effector actuator and an end effector both in a closed position.
Figure 16:
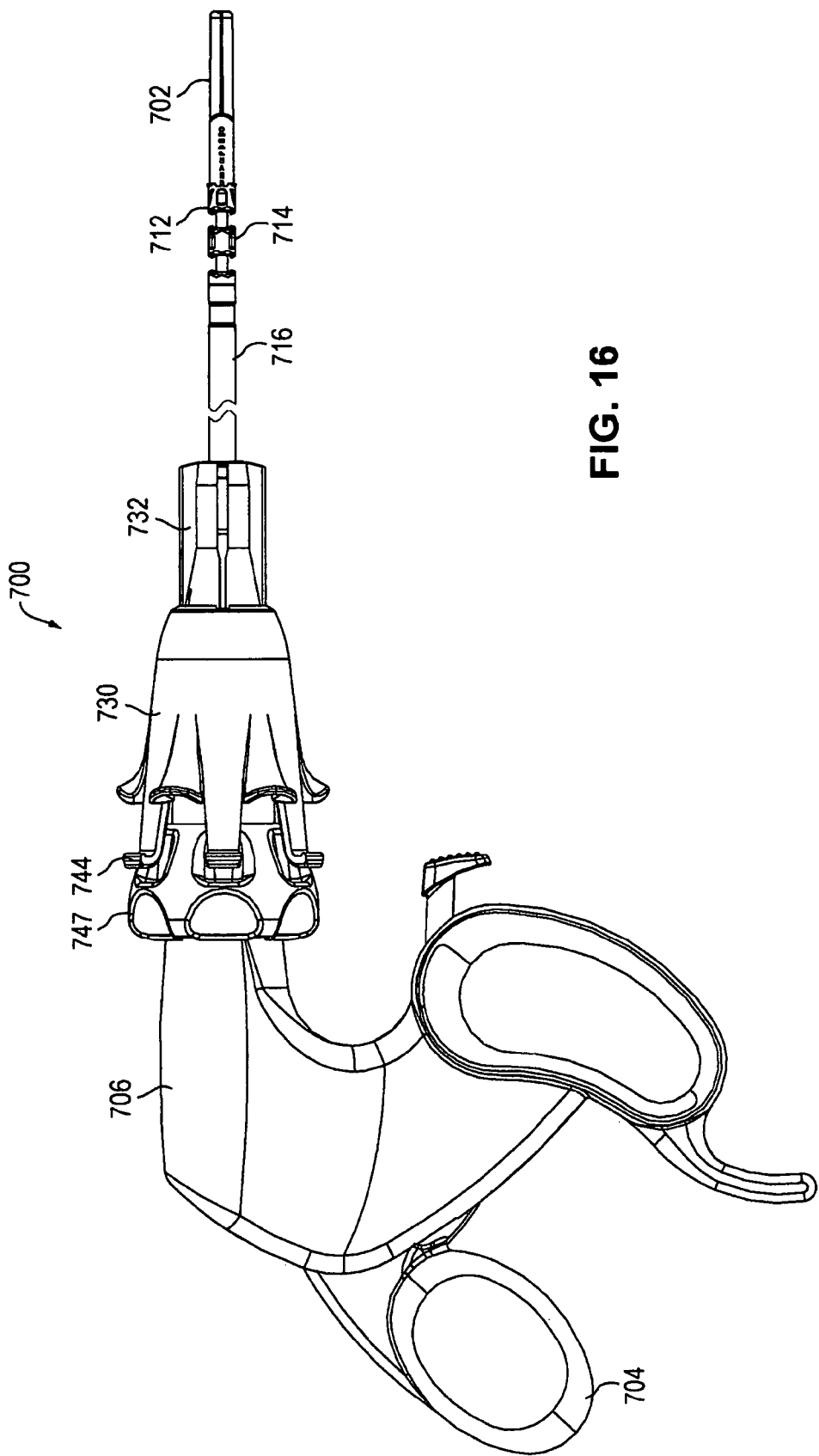
FIG. 16 is a side view of the embodiment shown in FIG. 15, but with the articulation locking sleeve in a proximal and locked position.

FIGS. 15-16 show another embodiment of the invention. Articulatable tool 700 has an end effector 702 at its distal end and an end effector actuator 704 within a handle 706 at its proximal end. Tool 700 may be used, e.g., in a laparoscopic procedure requiring grasping or cutting within a patient. Proximal articulation links 708 and 710 extend distally from handle 706, and distal articulation links 712 and 714 extend proximally from end effector 702. Proximal link 708 is connected to an moves with handle 706. Likewise, distal link 712 is connected to and moves with end effector 702. An elongated shaft 716 is disposed between the proximal links and the distal links. The linkage between pairs of proximal and distal links may be with cables as in the embodiment of FIG. 1 or by any other suitable means. Likewise, operation of end effector 702 may be as in the FIG. 1 embodiment.

As in the embodiment of FIGS. 1-14, movement of handle 706 and proximal link 708 with respect to proximal link 710 moves end effector 702 and distal link 712 in a relative and corresponding manner. Likewise, movement of proximal link 710 with respect to shaft link 716 moves distal link 714 with respect to shaft 716 in a relative and corresponding manner. This relative articulation movement provides a way for a user to remotely manipulate the end effector through movement of the handle.

In order to maintain a particular position of the end effector with respect to the shaft, the articulating tool of this embodiment has an articulation lock that controls the permissibility of angular movement between the distal portion of the tool and an end effector, if present there, with respect to the shaft. In the embodiment shown in FIGS. 15-16, the articulation lock includes a movable rigid sleeve 730. In the unlocked position shown in FIG. 15, sleeve 730 is distal to proximal links 708 and 710. In the locked position shown in FIG. 16, however, sleeve 730 has been moved proximally on sleeve support 732 to a position adjacent to and covering links 708 and 710 as well as the proximal end of shaft 716, thereby blocking relative movement between links 708 and 710 and between link 710 and shaft 716. In this locked position, relative movement between distal links 712 and 714 and between link 714 and shaft 716 is prevented as well.

Tool 700 has a rotation lock knob 747 that functions in a manner similar to that of FIGS. 1-14. When the device's articulation lock is in the locked position, pull tabs 744 nest with grooves 745 formed in the rotation lock knob 747.

Figure 17:
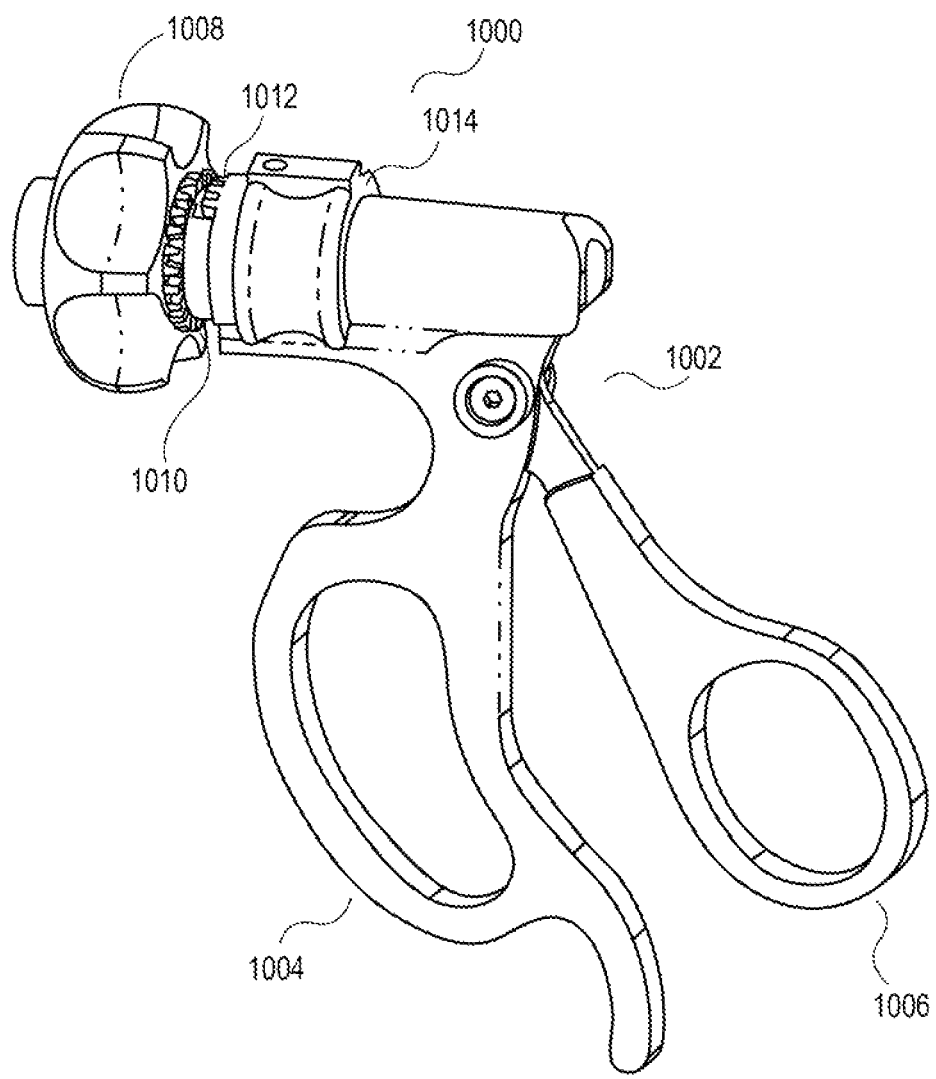
FIG. 17 is a side view of an embodiment of a tool with a rotation locking knob that is non-self locking, the rotation lock in an unlocked, disengaged proximal position.
Figure 18:
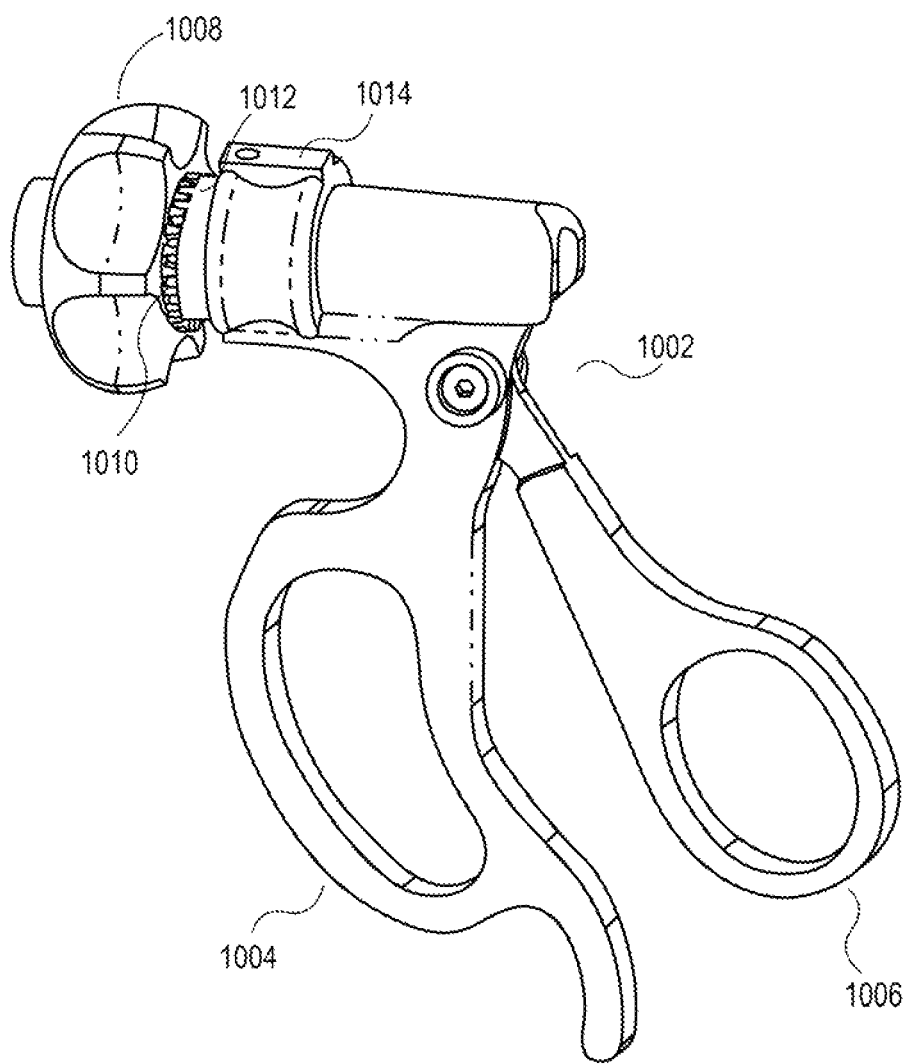
FIG. 18 is a side view of the embodiment shown in FIG. 17, but with the rotation lock in a locked or engaged position, the lock having been moved forward to a distal position.

FIGS. 17 and 18 illustrate another variation of the rotation knob, where the rotation knob is not-self locking. Shown there is a portion of a surgical instrument 1000. As with the surgical instruments described above, the surgical instrument 1000 of FIG. 17 has a handle 1002 having a stationary member 1004 and a movable member 1006. Also shown is a rotation knob 1008 having teeth 1010 for engaging with teeth 1012 on a sliding lock 1014. In this variation, there are only a few teeth 1012 on the sliding lock 1014, which was described above as an alternative, and it should be understood that the description of teeth above (and their alternatives such as pins, etc.) apply here as well.

The sliding lock 1014 is used to lock the rotation knob. Specifically, the sliding lock 1014 is moved distally or proximally, to engage, or disengage, as the case may be the teeth 1010 on rotation knob 1008 from teeth 1012 on sliding lock 1014. In its resting position, the sliding lock may be in either the locked or unlocked position, as will be described in more detail below. In FIG. 17, the sliding lock is shown in its unlocked, or disengaged, position. FIG. 18 shows the sliding lock in its locked, or engaged, position (e.g., after moving the sliding lock distally forward).

Figure 19:
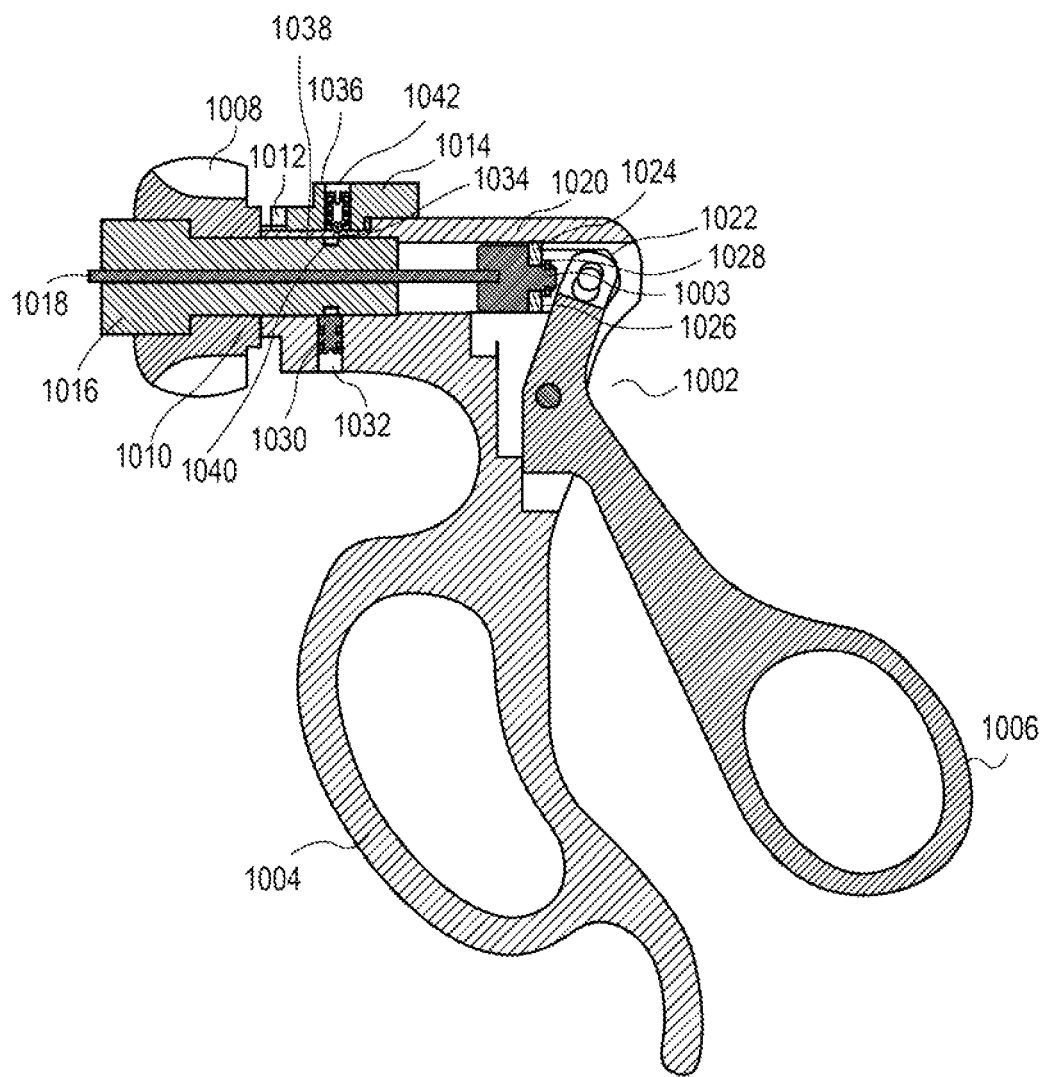
FIG. 19 is a cross sectional view of the embodiment shown in FIG. 17, with the locking rotation knob in its unlocked position.
Figure 20:
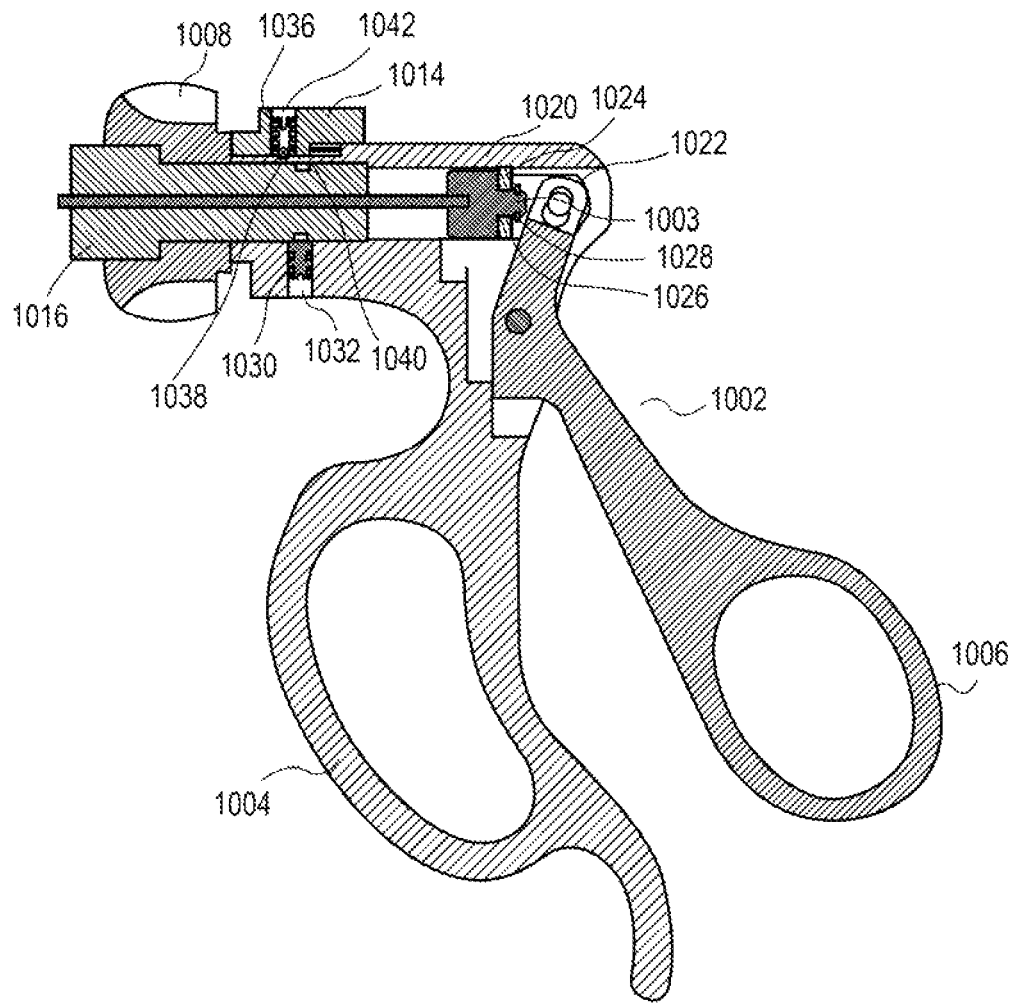
FIG. 20 is a cross sectional view of the embodiment shown in FIG. 17, with the locking rotation knob in its locked or engaged position.

FIG. 19 shows a cross-section of a portion of the surgical instrument 1000 of FIG. 17, where the rotation knob is in its unlocked position. Shown there is handle 1002 having stationary member 1004 and movable member 1006. Also shown is rotation knob 1008 with most proximal link 1016 sitting within a bore of rotation knob 1008. The proximal link 1016 may be fixedly engaged within or to rotation knob 1008, or may be integral with (e.g., manufactured as a single component) rotation knob 1008. As with the instruments comprising a self-locking rotation knob described above, the instrument here also has a push-pull wire 1018 to actuate the end effector (not shown). Termination piece 1020 of push-pull wire 1018 is rotatably connected to termination piece 1022 of handle 1002 at termination piece end 1024. Washer 1026 is placed around boss 1003 of termination piece 1020 and e-ring 1028 sits within a slot (not shown) on boss 1003. Also shown in a like fashion to the surgical instruments described above is dog-tipped set screw 1030 that is threaded within thread hole 1032 and engages circumferential slot 1034 on proximal link 1016. As described above, it should be understood that proximal link 1016 and push-pull wire 1018 can be rotatably connected to handle 1002 in other ways commonly known in the art. As can be seen in this cross-sectional view, the sliding lock 1014 does not sit around the entire circumference of the handle (although it may be designed as such if desirable). Ball plunger 1036 sits within and is attached to (e.g., screwed to) ball plunger hole 1042. The ball of ball plunger 1036 is shown sitting within proximal detent 1040. In this view, the sliding lock is in its unlocked, or disengaged position. When the sliding lock is pushed distally forward, the ball of ball plunger 1036 engages distal detent 1038 and maintains teeth 1010 of rotation knob 1008 and teeth 1012 of sliding lock 1014 in an engaged position, as shown in FIG. 20. It should also be understood that while ball plungers are described with reference to FIGS. 20 and 21, it should be understood that any suitable mechanism may be used to maintain the sliding lock 1014 in the engaged or disengaged position. For example, other plungers, buttons, and the like may be used.

Figure 21B:
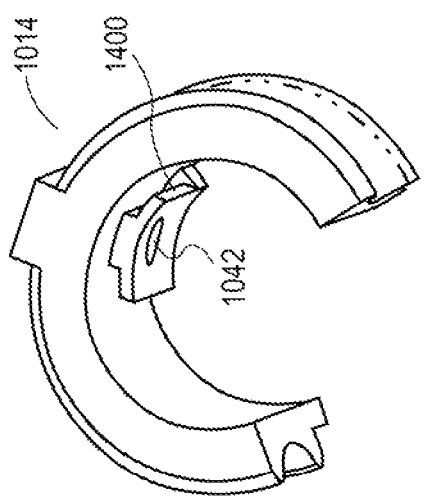
FIGS. 21A-C show various views of an exemplary sliding lock as shown in FIG. 17.
Figure 21C:
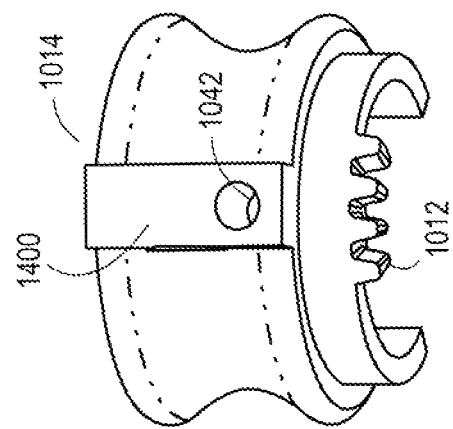
Figure 21A:
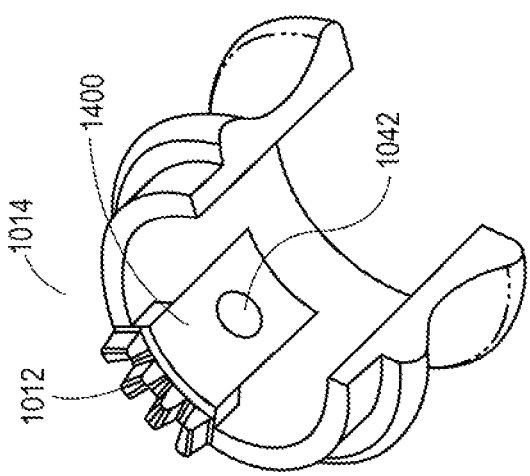

FIGS. 21A-21C show various views of an exemplary sliding lock 1014. Specifically, FIG. 21A shows a rotated front view, FIG. 21B shows a rotated end view, and FIG. 21C shows a top front view. Shown throughout the views are teeth 1012 for engaging with teeth on rotating knob 1008, ball plunger hole 1042 into which the ball plunger is secured, and flange 1400 for engaging within a slot (shown and described below with reference to FIG. 22) on the handle 1002. In this way, the sliding lock is able to slide axially, but is prevented from rotating. While the sliding lock shown here is generally semi-circular in geometry, any suitable geometry may be used.

Figure 22:
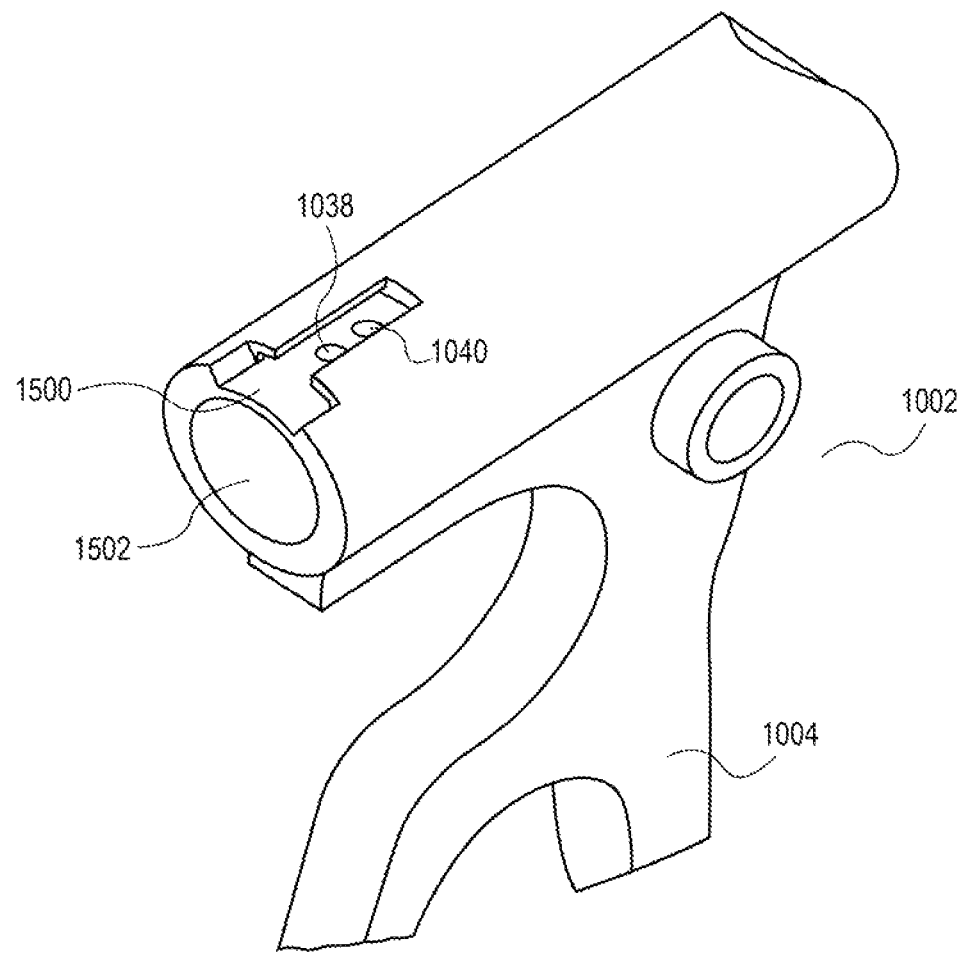
FIG. 22 is a partial cut-away view of the lock embodiment shown in FIG. 17, showing a portion of the handle.

FIG. 22 shows a partial cut-away view of a portion of handle 1002, having stationary member 1004. Also shown are distal 1038 and proximal 1040 detents for engaging and retaining the ball of ball plunger 1036. Slot 1500 is also shown. As mentioned briefly above, slot 1500 is configured to engage flange 1400 on sliding lock 1014. While the slot 1500 shown in FIG. 21 is configured to have a "T" shape, and corresponding flange 1400 is configured to have a corresponding "T" shape, the slot 1500 and flange 1400 need not have these geometries. Indeed, any suitable shapes may be used. Also shown in FIG. 22 is bore 1502 through which proximal link 1016 enters.

Figure 23:
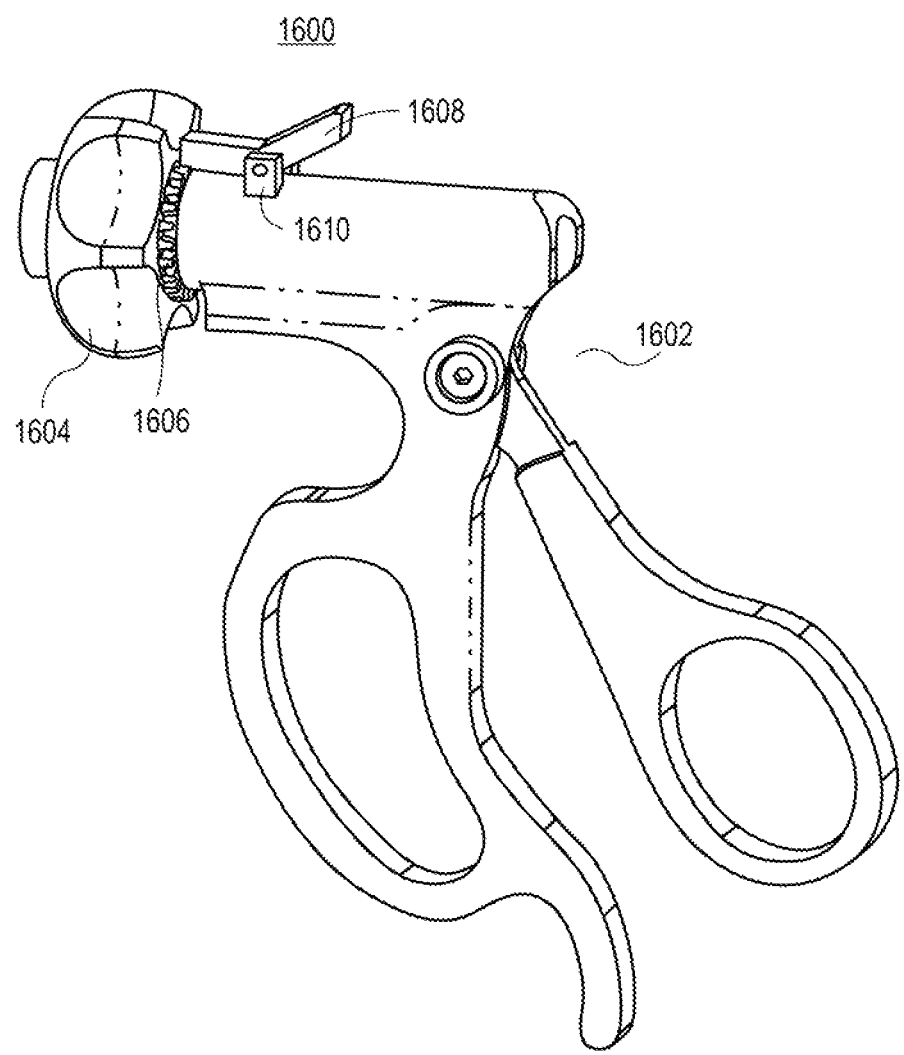
FIG. 23 is a perspective view of another embodiment of a non-self locking rotation lock comprising a trigger lock.

While various types of locking mechanisms have been just described (e.g., self-locking rotation knobs, sliding locks in combination with a rotation knob), it should be understood that any suitable locking mechanism may be used with the rotation knobs and surgical instruments described herein. For example, one alternative to a sliding lock used in combination with a rotation knob is the use of a trigger lock as shown in FIG. 23. Shown there is a proximal portion of surgical instrument 1600, comprising a handle 1602, a rotation knob 1604 having teeth 1606, and a trigger lock 1608. In this variation, the trigger lock 1608 is actuated by depressing the lock, which in turn disengages the teeth 1606 on rotation knob 1604 from teeth (not shown) on trigger lock 1608, or vice versa. Trigger lock 1608 is held in place by, and is pivotably connected to handle joint 1610. As with the variations described above, there may be any number of different variations on the acceptable teeth (or pins with holes, etc.). Similarly, the trigger lock may have any suitable geometry or configuration.

Figure 24:
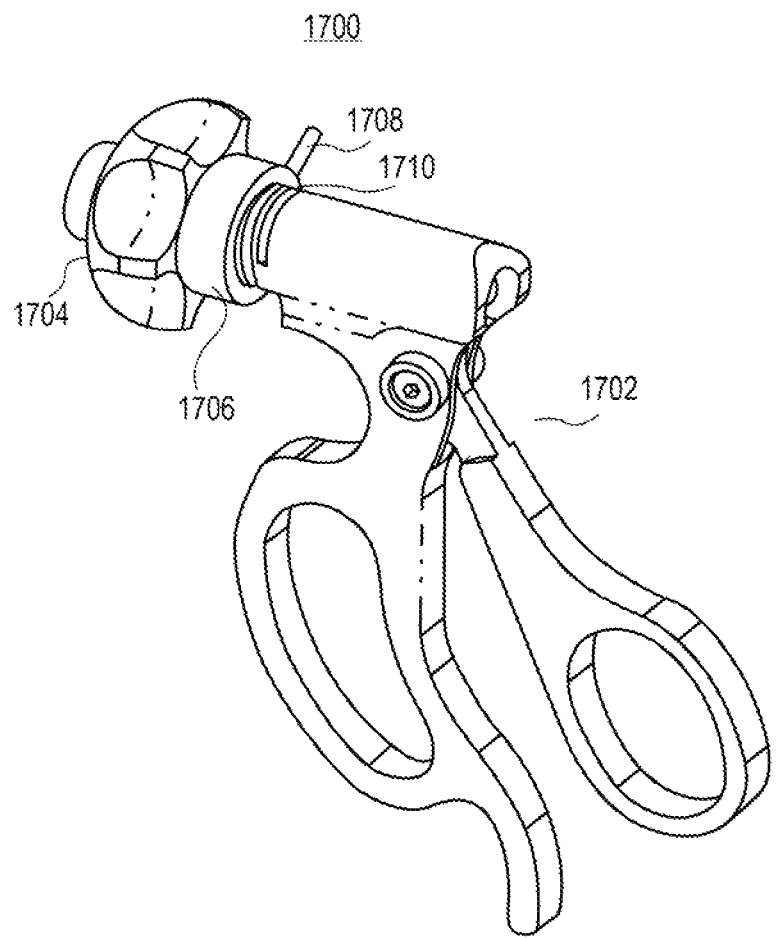
FIG. 24 is a perspective view of another embodiment of a non-self-locking rotation lock comprising a friction lock with a lever, with the lock in an engaged or locked position.
Figure 25:
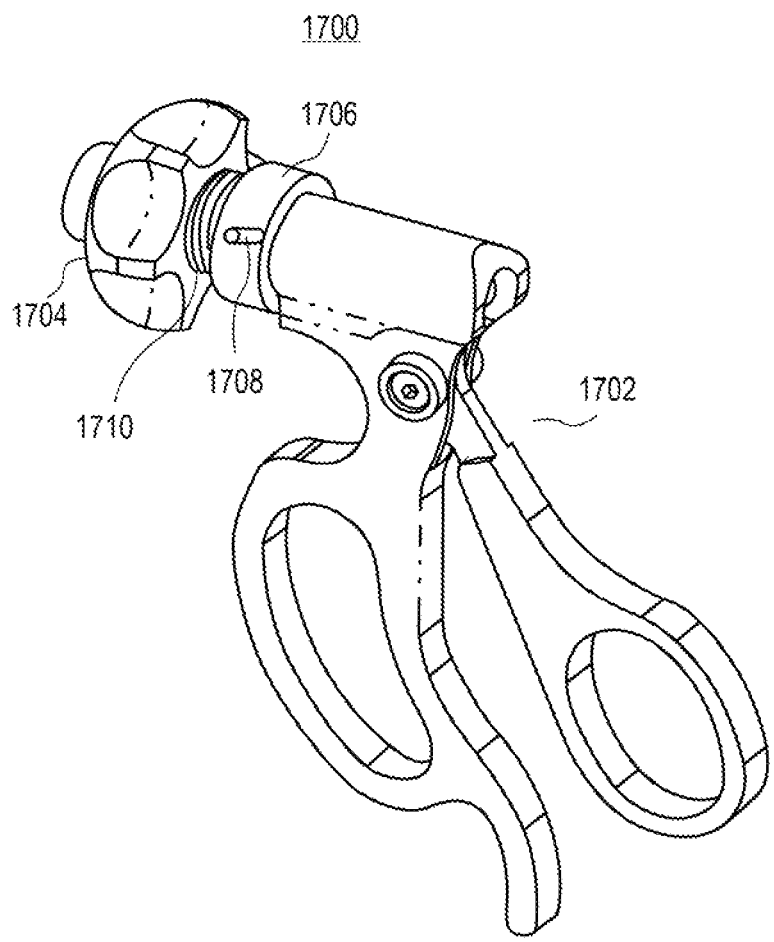
FIG. 25 is a perspective view of the embodiment shown in FIG. 24, where the lock has been rotated by use of the lever so that the friction lock has disengaged rotation knob in a proximal direction, thus unlocking rotation knob.

Another alternative to a sliding lock used in combination with a rotation knob is the use of a friction lock as shown in FIGS. 24 and 25. Shown in FIG. 24 is a proximal portion of surgical instrument 1700, comprising a handle 1702, a rotation knob 1704, and a friction lock 1706. The friction lock 1706 has a lever 1708, for moving the lock 1706 about threads 1710. Internal threads (not shown) on the friction lock 1706 engage threads 1710. When a user operates lever 1708 (e.g., with one or more fingers), the friction lock 1706 is rotated about threads 1710. In FIG. 24, the rotation knob 1704 is shown in its locked position. That is, friction lock 1706 is rotated about thread 1710 until it has engaged rotation knob 1704 locking it in place (like a brake or a clutch). Alternative methods of engaging the friction lock 1706 and rotation knob 1704 may also be used. For example, friction lock 1706 could be designed into a toggle clamp mounted to handle 1702. Other mechanisms known in the art may also be used. FIG. 25 shows the surgical instrument of FIG. 24 where the friction lock 1706 has been rotated by use of lever 1708 so that friction lock 1706 has disengaged rotation knob 1704 in a proximal direction, thus unlocking rotation knob 1704. It should be understood that while the trigger lock and friction lock described just above are suitable alternatives to a sliding lock, any suitable locking mechanism may be used to intermittently prevent rotation of the shaft and end effector.

FIGS. 26 and 27 show further details of spindle 117, which in the embodiment shown has a proximal link 108 formed on its distal end. As previously described, spindle 117 may be provided with fins 135 for rotationally fixing spindle 117 relative to knob 101 (as shown in FIG. 8). Spindle 117 may also be provided with bearing surface 1800 for allowing knob 101 to slide axially over spindle 117. Additionally, spindle 117 may be provided with bearing surface 1802 for allowing spindle 117 and proximal link 108 to rotate in handle 106 (as shown in FIG. 8). In this embodiment, spindle 117 is also provided with slot 1804 to permit axial loads to be transmitted from proximal link 108 to handle 106 (as also shown in FIG. 8). Through holes 1806 may be provided in link 108 for receiving the proximal ends of cables 118 (shown in FIG. 3) that interconnect proximal link 108 with distal link 112. In the embodiment shown in the figures, only three of the six holes 1806 of proximal link 108 are used to connect cables 118 to link 108. The proximal ends of cables 118 may be secured to link 108 by a variety of alternative processes as fully described in a concurrently filed and hereby incorporated U.S. patent application entitled "Articulating tool with improved tension member system" by Hegeman, et al.

While the inventive surgical instruments and devices have been described in some detail by way of illustrating the invention, such illustration is for purposes of clarity of understanding only. It will be readily apparent to those of ordinary skill in the art in light of the teachings herein that certain changes and modifications may be made thereto without departing from the spirit and scope of the appended claims. For example, while the rotation knobs described herein have typically been in the context of a tool with an articulating mechanism comprising at least two links, the rotation knobs may be used in an instrument comprising only a single link, a multiplicity of links, with any number of cables or cable sets operably connecting the links. Further, in some variations it may be desirable to have the handle affixed to a shaft, rigid or flexible, with or without a dedicated end effector. Further still, while the context of the invention is considered to be surgical or medical diagnostic procedures, embodiments of the rotation lock mechanism or tools having such a mechanism may have utility in non-medical contexts as well.

What is claimed is:

1. A device comprising:
 a proximal portion and a distal portion;
 a shaft interposed between the proximal portion and the distal portion;
 a handle at the proximal portion;
 an articulation mechanism for manipulating angular orientation of the distal portion, the articulation mechanism comprising proximal links on the proximal portion and distal links on the distal portion, each proximal link corresponding to one of the distal links to form pairs of links, wherein a bushing separates the first link of the proximal links from a second link of the proximal links and wherein movement of the proximal link of each pair causes corresponding relative movement of the distal link of the pair; and
 a shaft rotation lock defining a central axis extending therethrough in which a spindle is disposed, the spindle being fixed along the axis with respect to the handle and terminating in a first link of the proximal links, the spindle having an engaging slot configured to receive a proximal portion of the bushing therein, and wherein the shaft rotation lock is movable between a first state in which the articulation mechanism and distal portion are not rotatable with respect to the handle about the central axis and a second state in which the articulation mechanism and the distal portion are rotatable with respect to the handle about the central axis, the shaft rotation lock comprising a rotation member that is engaged with the articulation mechanism in the first and second states.

2. The device of claim 1, wherein the first link is disposed at a distal end of the spindle and a proximal end of the spindle has a chamber to receive a tension bearing member.

3. The device of claim 1 wherein the shaft rotation lock comprises a handle engagement surface engaged with the handle in the first state and not engaged with the handle in the second state.

4. The device of claim 3 wherein the handle engagement surface comprises a plurality of teeth and wherein the handle comprises a plurality of teeth adapted to engage with the handle engagement surface when the shaft rotation lock is in the first state.

5. The device of claim 4 wherein the handle further comprises a movable lock actuator supporting the plurality of teeth of the handle.

6. The device of claim 3 wherein the spindle is fixedly coupled to a most proximal link of the proximal links and is rotatably fixed relative to the rotation member in the first and second states.

7. The device of claim 6 wherein the rotation member is movable proximally and distally between the first state and the second state.

8. The device of claim 6 wherein the spindle includes fins engaged with the rotation member so that rotation of the rotation member rotates the articulation mechanism and the distal portion of the device with respect to the handle.

9. The device of claim 8 wherein the spindle cannot rotate with respect to the handle when the shaft rotation lock is in the first state.

10. The device of claim 1 wherein the shaft rotation lock is biased toward the first state.

11. The device of claim 10 wherein the shaft rotation lock comprises a spring biasing the shaft rotation lock toward the first state.

12. The device of claim 1 wherein the shaft rotation lock comprises a sliding engagement with a proximal link.

13. The device of claim 1 further comprising an articulation lock having an engaged position and a disengaged position, wherein in the engaged position the articulation lock impedes relative movement of the proximal links of each pair of links, thereby preventing relative movement of the distal link of each pair of links.

14. A method of using the device of claim 1; the method comprising:
placing the distal portion of the device of claim 1 at a target site;
moving the handle angularly with respect to the shaft to move the distal portion of the device angularly with respect to the shaft;
causing the shaft rotation lock to be in the second state;
with the shaft rotation lock in the second state, rotating the handle with respect to the shaft without rotating the distal portion; and
with the shaft rotation lock in the first state, applying rotational torque to the distal portion by rotating the handle about the central axis.

15. The method of claim 14 wherein the device comprises a surgical or diagnostic tool.

16. The method of claim 14 wherein the device further comprises an end effector disposed at the distal portion of the device.

17. The method of claim 14 wherein the shaft rotation lock further comprises a rotation member, and wherein the step of rotating the handle with respect to the shaft comprises moving the rotation member from a first position to a second position.

18. The method of claim 17 further comprising moving the rotation member from the second position to the first position prior to the step of applying rotational torque to the distal portion.

19. The method of claim 17 wherein rotating the handle with respect to the shaft comprises rotating the handle with respect to the rotation member.

20. The method of claim 17 wherein rotating the handle with respect to the shaft comprises rotating the handle with respect to the rotation member while the rotation member is in the second position.

21. The method of claim 17 wherein the first position is proximal to the second position.

22. The method of claim 14 further comprising controlling permissibility of relative angular movement between the handle and the shaft.

23. The method of claim 22 wherein controlling permissibility of angular movement comprises impeding angular movement by moving an articulation lock from a disengaged position to an engaged position, wherein in the engaged position the articulation lock impedes movement of at least one of the proximal links and corresponding relative movement of at least one of the distal links.

24. The method of claim 23 wherein the articulation lock comprises a sleeve, and the step of moving the articulation lock comprising sliding the sleeve.

25. The method of claim 24 wherein the step of moving the articulation lock comprises sliding the sleeve proximally along the device.

26. The method of claim 23 wherein controlling permissibility of angular movement comprises permitting angular movement by moving the articulation lock from the engaged position to the disengaged position to permit relative angular movement between the handle and the shaft.

27. A device comprising:
a proximal portion and a distal portion;
a shaft interposed between the proximal portion and the distal portion, a proximal portion of the shaft including an articulation lock support mechanism;
a handle at the proximal portion;
an articulation mechanism for manipulating angular orientation of the distal portion, the articulation mechanism comprising proximal links on the proximal portion and distal links on the distal portion, each proximal link corresponding to one of the distal links to form pairs of links, wherein movement of the proximal link of each pair causes corresponding relative movement of the distal link of the pair;
a shaft rotation lock defining a central axis extending therethrough and movable between a first state in which the articulation mechanism and distal portion are not rotatable with respect to the handle about the central axis and a second state in which the articulation mechanism and the distal portion are rotatable with respect to the handle about the central axis; and
an articulation lock having an engaged position and a disengaged position, wherein in the engaged position the articulation lock engages at least two proximal links to impede the relative movement of the proximal links, thereby preventing relative movement of the distal links, and wherein in the disengaged position the articulation lock is supported by the articulation lock support mechanism.

28. The device of claim 27 wherein the device comprises a bushing separating a first link of the distal links from a second link of the distal links.

29. The device of claim 27 wherein further comprising an end effector disposed at the distal portion of the device.

30. The device of claim 27 wherein the shaft rotation lock comprises a handle engagement surface engaged with the handle in the first state and not engaged with the handle in the second state.

31. The device of claim 30 wherein the handle engagement surface comprises a plurality of teeth and wherein the handle comprises a plurality of teeth adapted to engage with the handle engagement surface when the shaft rotation lock is in the first state.

32. The device of claim 30 wherein the shaft rotation lock further comprises a rotation member that is engaged with the articulation mechanism in the first and second states.

33. The device of claim 32 wherein the rotation member is movable proximally and distally between the first state and the second state.

34. The device of claim 32 wherein the shaft rotation lock further comprises a spindle coupled to the rotation member and engaged with the articulation mechanism such that rotation of the spindle rotates the articulation mechanism and the distal portion of the device with respect to the handle.

35. The device of claim 34 wherein the spindle cannot rotate with respect to the handle when the shaft rotation lock is in the first state.

36. The device of claim 27 wherein the shaft rotation lock is biased toward the first state.

37. The device of claim 36 wherein the shaft rotation lock comprises a spring biasing the shaft rotation mechanism toward the first state.

38. The device of claim 27 wherein the articulation mechanism comprises a plurality of pairs of proximal and distal links, such that movement of the proximal link of each pair causes corresponding relative movement of the distal link of the pair and angular movement of the distal portion with respect to the shaft.

39. The device of claim 27 wherein the shaft rotation lock comprises a sliding engagement with a proximal link.

40. A method of using the device of claim 27, the method comprising:

placing the distal portion of the device of claim 27 at a target site;
moving the handle angularly with respect to the shaft to move the distal portion of the device angularly with respect to the shaft;
causing the shaft rotation lock to be in the second state;
rotating the handle with respect to the shaft without rotating the distal portion;
causing the shaft rotation lock to be in the first state; and
applying rotational torque to the distal portion by rotating the handle about the central axis.

* * * * *